(12) United States Patent
Chung et al.

(10) Patent No.: US 10,568,507 B2
(45) Date of Patent: Feb. 25, 2020

(54) PUPIL PTYCHOGRAPHY METHODS AND SYSTEMS

(71) Applicant: California Institute of Technology, Pasadena, CA (US)

(72) Inventors: Jaebum Chung, Pasadena, CA (US); Changhuei Yang, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/620,674

(22) Filed: Jun. 12, 2017

(65) Prior Publication Data

US 2017/0354329 A1    Dec. 14, 2017

Related U.S. Application Data

(60) Provisional application No. 62/348,433, filed on Jun. 10, 2016.

(51) Int. Cl.
| | | |
|---|---|---|
| *A61B 3/14* | (2006.01) | |
| *A61B 3/12* | (2006.01) | |
| *A61B 3/00* | (2006.01) | |

(52) U.S. Cl.
CPC ............ *A61B 3/14* (2013.01); *A61B 3/0025* (2013.01); *A61B 3/12* (2013.01)

(58) Field of Classification Search
CPC .................................. A61B 3/14; A61B 3/13
See application file for complete search history.

(56) References Cited

U.S. PATENT DOCUMENTS

| | | |
|---|---|---|
| 5,475,527 A | 12/1995 | Hackel et al. |
| 6,144,365 A | 11/2000 | Young et al. |
| 6,154,196 A | 11/2000 | Fleck et al. |
| 6,320,174 B1 | 11/2001 | Tafas et al. |
| 6,320,648 B1 | 11/2001 | Brueck et al. |
| 6,747,781 B2 | 6/2004 | Trisnadi |
| 6,759,949 B2 | 7/2004 | Miyahara |
| 6,905,838 B1 | 6/2005 | Bittner |
| 7,436,503 B1 | 10/2008 | Chen et al. |
| 7,460,248 B2 | 12/2008 | Kurtz et al. |
| 7,706,419 B2 | 4/2010 | Wang et al. |
| 7,738,095 B2 | 6/2010 | Gardner, Jr. et al. |
| 7,787,588 B1 | 8/2010 | Yun et al. |
| 8,271,251 B2 | 9/2012 | Schwartz et al. |
| 8,313,031 B2 | 11/2012 | Vinogradov |
| 8,497,934 B2 | 7/2013 | Milnes et al. |
| 8,624,968 B1 | 1/2014 | Hersee et al. |

(Continued)

FOREIGN PATENT DOCUMENTS

| | | |
|---|---|---|
| CN | 1688254 A | 10/2005 |
| CN | 1932565 A | 3/2007 |

(Continued)

OTHER PUBLICATIONS

Preliminary Amendment dated Mar. 17, 2014 filed in U.S. Appl. No. 14/065,280.

(Continued)

*Primary Examiner* — Nam D Pham
(74) *Attorney, Agent, or Firm* — Sheila Martinez-Lemke; Weaver Austin Villeneuve & Sampson LLP

(57) ABSTRACT

Certain embodiments pertain to pupil ptychography methods and systems.

18 Claims, 6 Drawing Sheets

(56) References Cited

U.S. PATENT DOCUMENTS

| | | |
|---|---|---|
| 8,654,201 B2 | 2/2014 | Lim et al. |
| 8,942,449 B2 | 1/2015 | Maiden |
| 9,029,745 B2 | 5/2015 | Maiden |
| 9,426,455 B2 | 8/2016 | Horstmeyer et al. |
| 9,497,379 B2 | 11/2016 | Ou et al. |
| 9,829,695 B2 | 11/2017 | Kim et al. |
| 9,864,184 B2 | 1/2018 | Ou et al. |
| 9,892,812 B2 | 2/2018 | Zheng et al. |
| 9,983,397 B2 | 5/2018 | Horstmeyer et al. |
| 9,993,149 B2 | 6/2018 | Chung et al. |
| 9,998,658 B2 | 6/2018 | Ou et al. |
| 10,162,161 B2 | 12/2018 | Horstmeyer et al. |
| 10,168,525 B2 | 1/2019 | Kim et al. |
| 10,222,605 B2 | 3/2019 | Kim et al. |
| 10,228,550 B2 | 3/2019 | Ou et al. |
| 10,401,609 B2 | 9/2019 | Ou et al. |
| 10,419,665 B2 | 9/2019 | Ou et al. |
| 2001/0055062 A1 | 12/2001 | Shioda et al. |
| 2002/0141051 A1 | 10/2002 | Vogt et al. |
| 2003/0116436 A1 | 6/2003 | Amirkhanian et al. |
| 2003/0118223 A1 | 6/2003 | Rahn et al. |
| 2004/0057094 A1 | 3/2004 | Olszak et al. |
| 2004/0146196 A1 | 7/2004 | Van Heel |
| 2004/0190762 A1 | 9/2004 | Dowski, Jr. et al. |
| 2005/0211912 A1 | 9/2005 | Fox |
| 2006/0098293 A1 | 5/2006 | Garoutte et al. |
| 2006/0158754 A1 | 7/2006 | Tsukagoshi et al. |
| 2006/0173313 A1 | 8/2006 | Liu et al. |
| 2006/0291707 A1 | 12/2006 | Kothapalli et al. |
| 2007/0057184 A1 | 3/2007 | Uto et al. |
| 2007/0133113 A1 | 6/2007 | Minabe et al. |
| 2007/0159639 A1 | 7/2007 | Teramura et al. |
| 2007/0171430 A1 | 7/2007 | Tearney et al. |
| 2007/0189436 A1 | 8/2007 | Goto et al. |
| 2007/0206200 A1 | 9/2007 | Lindner et al. |
| 2007/0269826 A1 | 11/2007 | Geddes |
| 2008/0101664 A1 | 5/2008 | Perez |
| 2008/0182336 A1 | 7/2008 | Zhuang et al. |
| 2009/0046164 A1 | 2/2009 | Shroff et al. |
| 2009/0079987 A1 | 3/2009 | Ben-Ezra et al. |
| 2009/0125242 A1 | 5/2009 | Choi et al. |
| 2009/0284831 A1 | 11/2009 | Schuster et al. |
| 2009/0316141 A1 | 12/2009 | Feldkhun |
| 2010/0135547 A1 | 6/2010 | Lee et al. |
| 2010/0271705 A1 | 10/2010 | Hung |
| 2011/0075928 A1 | 3/2011 | Jeong et al. |
| 2011/0181869 A1 | 7/2011 | Yamaguchi et al. |
| 2011/0192976 A1 | 8/2011 | Own et al. |
| 2011/0235863 A1 | 9/2011 | Maiden |
| 2011/0255163 A1 | 10/2011 | Merrill et al. |
| 2012/0069344 A1 | 3/2012 | Liu |
| 2012/0099803 A1 | 4/2012 | Ozcan et al. |
| 2012/0105618 A1 | 5/2012 | Brueck et al. |
| 2012/0118967 A1 | 5/2012 | Gerst |
| 2012/0157160 A1 | 6/2012 | Ozcan et al. |
| 2012/0176673 A1 | 7/2012 | Cooper |
| 2012/0218379 A1 | 8/2012 | Ozcan et al. |
| 2012/0248292 A1 | 10/2012 | Ozcan et al. |
| 2012/0250032 A1 | 10/2012 | Wilde et al. |
| 2012/0281929 A1 | 11/2012 | Brand et al. |
| 2013/0057748 A1 | 3/2013 | Duparre et al. |
| 2013/0083886 A1 | 4/2013 | Carmi et al. |
| 2013/0093871 A1 | 4/2013 | Nowatzyk et al. |
| 2013/0094077 A1 | 4/2013 | Brueck et al. |
| 2013/0100525 A1 | 4/2013 | Chiang et al. |
| 2013/0170767 A1 | 7/2013 | Choudhury et al. |
| 2013/0182096 A1 | 7/2013 | Boccara et al. |
| 2013/0223685 A1 | 8/2013 | Maiden |
| 2014/0007307 A1 | 1/2014 | Routh, Jr. et al. |
| 2014/0029824 A1 | 1/2014 | Shi et al. |
| 2014/0043616 A1 | 2/2014 | Maiden et al. |
| 2014/0050382 A1 | 2/2014 | Adie et al. |
| 2014/0085629 A1 | 3/2014 | Bodkin et al. |
| 2014/0118529 A1 | 5/2014 | Zheng et al. |
| 2014/0126691 A1 | 5/2014 | Zheng et al. |
| 2014/0133702 A1 | 5/2014 | Zheng et al. |
| 2014/0152801 A1 | 6/2014 | Fine et al. |
| 2014/0153692 A1 | 6/2014 | Larkin et al. |
| 2014/0160236 A1 | 6/2014 | Ozcan et al. |
| 2014/0160488 A1 | 6/2014 | Zhou |
| 2014/0217268 A1 | 8/2014 | Schleipen et al. |
| 2014/0267674 A1 | 9/2014 | Mertz et al. |
| 2014/0347672 A1 | 11/2014 | Pavillon et al. |
| 2014/0368812 A1 | 12/2014 | Humphry et al. |
| 2015/0036038 A1 | 2/2015 | Horstmeyer et al. |
| 2015/0054979 A1 | 2/2015 | Ou et al. |
| 2015/0160450 A1 | 6/2015 | Ou et al. |
| 2015/0264250 A1 | 9/2015 | Ou et al. |
| 2015/0286042 A1 | 10/2015 | Hilbert et al. |
| 2015/0331228 A1 | 11/2015 | Horstmeyer et al. |
| 2016/0088205 A1 | 3/2016 | Horstmeyer et al. |
| 2016/0110584 A1 | 4/2016 | Remiszewski et al. |
| 2016/0156880 A1 | 6/2016 | Teich et al. |
| 2016/0178883 A1 | 6/2016 | Horstmeyer et al. |
| 2016/0202460 A1 | 7/2016 | Zheng |
| 2016/0210763 A1 | 7/2016 | Horstmeyer et al. |
| 2016/0216208 A1 | 7/2016 | Kim et al. |
| 2016/0216503 A1 | 7/2016 | Kim et al. |
| 2016/0266366 A1 | 9/2016 | Chung et al. |
| 2016/0320595 A1 | 11/2016 | Horstmeyer et al. |
| 2016/0320605 A1 | 11/2016 | Ou et al. |
| 2016/0341945 A1 | 11/2016 | Ou et al. |
| 2017/0061599 A1 | 3/2017 | Remiszewski et al. |
| 2017/0146788 A1 | 5/2017 | Waller et al. |
| 2017/0178317 A1 | 6/2017 | Besley et al. |
| 2017/0188853 A1* | 7/2017 | Nakao .................. A61B 5/0066 |
| 2017/0273551 A1 | 9/2017 | Chung et al. |
| 2017/0299854 A1 | 10/2017 | Kim et al. |
| 2017/0354329 A1 | 12/2017 | Chung et al. |
| 2017/0363853 A1 | 12/2017 | Besley |
| 2017/0371141 A1 | 12/2017 | Besley |
| 2018/0048811 A1 | 2/2018 | Waller et al. |
| 2018/0088309 A1 | 3/2018 | Ou et al. |
| 2018/0231761 A1 | 8/2018 | Dai et al. |
| 2018/0307017 A1 | 10/2018 | Horstmeyer et al. |
| 2018/0316855 A1 | 11/2018 | Ou et al. |
| 2019/0049712 A1 | 2/2019 | Kim et al. |
| 2019/0056578 A1 | 2/2019 | Horstmeyer et al. |
| 2019/0137753 A1 | 5/2019 | Chan et al. |
| 2019/0317311 A1 | 10/2019 | Kim et al. |
| 2019/0331902 A1 | 10/2019 | Ou et al. |

FOREIGN PATENT DOCUMENTS

| | | |
|---|---|---|
| CN | 1311392 C | 4/2007 |
| CN | 101408623 A | 4/2009 |
| CN | 101680848 A | 3/2010 |
| CN | 101743519 A | 6/2010 |
| CN | 101868740 A | 10/2010 |
| CN | 101872033 A | 10/2010 |
| CN | 101957183 A | 1/2011 |
| CN | 102608597 A | 7/2012 |
| CN | 102753935 A | 10/2012 |
| CN | 103096804 A | 5/2013 |
| CN | 103154662 A | 6/2013 |
| CN | 103201648 A | 7/2013 |
| CN | 103377746 A | 10/2013 |
| CN | 104181686 A | 12/2014 |
| CN | 104200449 A | 12/2014 |
| JP | 2007-299604 A | 11/2007 |
| JP | 2008-147629 A | 6/2008 |
| JP | 2010-012222 A | 1/2010 |
| KR | 10-1998-0075050 A | 11/1998 |
| TW | 201428339 A | 7/2014 |
| WO | WO 99/53469 A1 | 10/1999 |
| WO | WO 2002/102128 A1 | 12/2002 |
| WO | WO 2003/062744 A1 | 7/2003 |
| WO | WO 2008/116070 A1 | 9/2008 |
| WO | WO 2011/093043 A1 | 8/2011 |
| WO | WO 2012/037182 A1 | 3/2012 |
| WO | WO 2014/070656 A1 | 5/2014 |
| WO | WO 2015/017730 A1 | 2/2015 |
| WO | WO 2015/027188 A1 | 2/2015 |
| WO | WO 2016/090331 A1 | 6/2016 |

(56) References Cited

FOREIGN PATENT DOCUMENTS

| WO | WO 2016/106379 A1 | 6/2016 |
|---|---|---|
| WO | WO 2016/118761 A1 | 7/2016 |
| WO | WO 2016/123156 A1 | 8/2016 |
| WO | WO 2016/123157 A1 | 8/2016 |
| WO | WO 2016/149120 A1 | 9/2016 |
| WO | WO 2016/187591 A1 | 11/2016 |
| WO | WO 2017/066198 A1 | 4/2017 |
| WO | WO 2017081539 A1 | 5/2017 |
| WO | WO 2017081540 A1 | 5/2017 |
| WO | WO 2017081542 A2 | 5/2017 |

OTHER PUBLICATIONS

Preliminary Amendment dated Apr. 25, 2016 filed in U.S. Appl. No. 14/710,947.
Preliminary Amendment dated Nov. 28, 2016 filed in U.S. Appl. No. 15/206,859.
Preliminary Amendment dated Mar. 17, 2014 filed in U.S. Appl. No. 14/065,305.
Preliminary Amendment dated Nov. 28, 2016 filed in U.S. Appl. No. 15/209,604.
U.S. Office Action dated Oct. 5, 2015 in U.S. Appl. No. 14/065,305.
U.S. Notice of Allowance dated Dec. 4, 2015 in U.S. Appl. No. 14/065,305.
U.S. Notice of Allowance dated Jan. 14, 2016 in U.S. Appl. No. 14/448,850.
U.S. Notice of Allowance dated Jan. 22, 2016 in U.S. Appl. No. 14/466,481.
U.S. Notice of Allowance dated Apr. 13, 2016 in U.S. Appl. No. 14/448,850.
U.S. Notice of Allowance dated Apr. 22, 2016 in U.S. Appl. No. 14/466,481.
U.S. Office Action dated Jul. 14, 2016 in U.S. Appl. No. 15/007,196.
U.S. Notice of Allowance dated Aug. 23, 2016 in U.S. Appl. No. 14/466,481.
U.S. Office Action dated Aug. 16, 2016 in U.S. Appl. No. 14/065,280.
U.S. Office Action dated Sep. 16, 2016 I U.S. Appl. No. 14/065,305.
U.S. Notice of Allowance dated Nov. 2, 2016 in U.S. Appl. No. 14/572,493.
U.S. Office Action dated Nov. 22, 2016 in U.S. Appl. No. 15/003,559.
U.S. Supplemental Notice of Allowance dated Dec. 12, 2016 in U.S. Appl. No. 14/572,493.
U.S. Notice of Allowance dated Jan. 13, 2017 in U.S. Appl. No. 14/065,305.
U.S. Final Office Action dated Jan. 23, 2017 in U.S. Appl. No. 15/007,196.
U.S. Office Action dated Feb. 21, 2017 in U.S. Appl. No. 14/960,252.
U.S. Notice of Allowance dated Mar. 8, 2017 in U.S. Appl. No. 14/572,493.
U.S. Office Action dated Mar. 13, 2017 in U.S. Appl. No. 14/658,019.
U.S. Notice of Allowance dated Mar. 22, 2017 in U.S. Appl. No. 15/007,196.
U.S. Office Action dated Mar. 24, 2017 in U.S. Appl. No. 14/710,947.
U.S. Notice of Allowance dated Mar. 31, 2017 in U.S. Appl. No. 14/572,493.
U.S. Final Office Action dated Apr. 3, 2017 in U.S. Appl. No. 14/065,280.
U.S. Notice of Allowance dated Jun. 9, 2017 in U.S. Appl. No. 14/065,305.
U.S. Notice of Allowance dated Jun. 9, 2017 in U.S. Appl. No. 15/206,859.
U.S. Notice of Allowance dated Jun. 9, 2017 in U.S. Appl. No. 15/007,196.
U.S. Notice of Allowance dated Jun. 20, 2017 in U.S. Appl. No. 14/572,493.
U.S. Supplemental Notice of Allowance dated Jun. 28, 2017 in U.S. Appl. No. 15/206,859.
U.S. Final Office Action dated Jul. 27, 2017 in U.S. Appl. No. 15/003,559.
U.S. Notice of Allowance dated Aug. 16, 2017 in U.S. Appl. No. 15/209,604.
Office Action dated Aug. 31, 2017 in U.S. Appl. No. 15/636,494.
U.S. Notice of Allowance dated Sep. 1, 2017 in U.S. Appl. No. 15/206,859.
Office Action dated May 19, 2017 in U.S. Appl. No. 15/081,659.
Notice of Allowance dated Sep. 20, 2017 in U.S. Appl. No. 15/007,196.
Notice of Allowance dated Oct. 11, 2017 in U.S. Appl. No. 14/572,493.
Notice of Allowance dated Oct. 20, 2017 in U.S. Appl. No. 15/081,659.
Office Action dated Nov. 3, 2017 in U.S. Appl. No. 15/068,389.
Office Action dated Nov. 30, 2017 in U.S. Appl. No. 15/007,159.
Notice of Allowance dated Dec. 4, 2017 in U.S. Appl. No. 14/065,305.
Final Office Action dated Dec. 14, 2017 in U.S. Appl. No. 14/960,252.
Final Office Action dated Dec. 28, 2017 in U.S. Appl. No. 14/710,947.
Final Office Action dated Jan. 17, 2018 in U.S. Appl. No. 14/658,019.
Notice of Allowance dated Jan. 23, 2018 in U.S. Appl. No. 15/206,859.
Office Action dated Jan. 25, 2018 in U.S. Appl. No. 14/065,280.
Notice of Allowance dated Jan. 26, 2018 in U.S. Appl. No. 15/209,604.
International Search Report and Written Opinion dated Feb. 21, 2014 in PCT/US2013/067068.
International Preliminary Report on Patentability dated May 14, 2015 in PCT/US2013/067068.
European Third-Party Observations, dated Jan. 20, 2016 in EP Application No. 13851670.3.
European Extended Search Report dated Mar. 31, 2016 in EP Application No. 13851670.3.
International Preliminary Report on Patentability dated Mar. 3, 2016 issued in PCT/US2014/052351.
International Search Report and Written Opinion dated Dec. 5, 2014 issued in PCT/US2014/052351.
International Search Report and Written Opinion dated Nov. 13, 2014 issued in PCT/US2014/049297.
International Preliminary Report on Patentability dated Feb. 11, 2016 issued in PCT/US2014/049297.
International Search Report and Written Opinion dated Feb. 22, 2016 issued in PCT/US2015/064126.
International Search Report and Written Opinion dated Apr. 19, 2016 issued in PCT/US2015/067498.
International Search Report and Written Opinion dated May 4, 2016 issued in PCT/US2016/015001.
International Search Report and Written Opinion dated May 11, 2016 issued in PCT/US2016/015002.
International Search Report and Written Opinion dated Jun. 27, 2016 issued in PCT/US2016/022116.
International Search Report and Written Opinion dated Jun. 30, 2016 issued in PCT/US2016/014343.
International Search Report and Wrtitten Opinion dated Sep. 5, 2016 issued in PCT/US2016/033638.
Chinese Office Action [Description in English] dated May 31, 2016 issued in Application No. CN 201380068831.6.
Chinese Office Action dated Dec. 13, 2016 issued in Application No. CN201480057911.6.
Extended European Search Report dated Feb. 16, 2017 issued in Application No. 14837844.1.
Extended European Search Report dated Feb. 15, 2017 issued in Applicatoin No. 14832857.8.
Chinese Second Office Action [Description in English] dated Jan. 22, 2017 issued in Application No. CN201380068831.6.
International Preliminary Report on Patentability dated Jun. 15, 2017 issued in Application No. PCT/US2015/064126.
European Office Action dated May 16, 2017 issued in European Patent Application No. 13851670.3.
International Preliminary Report on Patentability dated Jul. 6, 2017 issued in Application No. PCT/US2015/067498.
International Preliminary Report on Patentability dated Aug. 3, 2017 issued in Application No. PCT/US2016/014343.
International Preliminary Report on Patentability dated Aug. 10, 2017 issued in Application No. PCT/US2016/015001.
International Preliminary Report on Patentability dated Aug. 10, 2017 issued in Application No. PCT/US2016/015002.

(56) References Cited

OTHER PUBLICATIONS

Chinese Third Office Action [Summary in English] dated Jul. 24, 2017 issued in Application No. 201380068831.6.
Chinese First Office Action [Summary in English] dated Aug. 2, 2017 issued in Application No. CN 201480054301.0.
Australian Office Action dated Sep. 18, 2017 issued in Application No. AU 2014296034.
International Preliminary Report on Patentability dated Sep. 28, 2017 issued in Application No. PCT/US2016/022116.
Japanese Office Action dated Oct. 17, 2017 issued in Application No. 2015-539884.
Chinese Office Action [Summary in English] dated Oct. 26, 2017 issued in CN 201480057911.6.
International Preliminary Report on Patentability dated Nov. 30, 2017 issued in PCT/US2016/033638.
About Molemap, About Us-Skin Cancer Mole Check NZ, pp. 1-2. [retrieved Oct. 23, 2015 ] <URL: http://molemap.net.au/about-us/>.
Abrahamsson, S., et al., "Fast multicolor 3D imaging using aberration-corrected mulitfocus microscopy," Brief Communications: Nature Methods, vol. 10, No. 1, Jan. 2013, pp. 60-65. <doi:10.1038/nmeth.2277>.
Abramowitz, M. et al, "Immersion Media," Olympus Microscopy Resource Center: Microscope Optical Components, Published 2012, pp. 1-6.[retrieved on Feb. 6, 2012] <URL: http://www.olympusmicro.com/primer/anatomy/immersion.html>.
Abramowitz, M., et al, "Field Curvature," Olympus Microscopy Resource Center, 2012 Olympus America Inc., pp. 1-3. [retrieved on Feb. 24, 2016] <URL:http://www.olympusmicro.com/primer/anatomy/fieldcurvature.html>.
Age-Related Macular Degeneration (AMD) | National Eye Institute. 2010 Table, pp. 1-8. [retrieved Apr. 5, 2016] <URL: https://www.nei.nih.gov/eyedata/amd#top>.
Alexandrov, S., et al, "Spatial information transmission beyond a system's diffraction limit using optical spectral encoding of the spatial frequency," Journal of Optics A: Pure and Applied Optics 10, Feb. 4, 2008, 025304, pp. 1-5. <doi: 10.1088/1464-4258/10/2/025304> [retrieved Dec. 2, 2015] <URL: http://www.stacks.iop.org/JOptA/10/025304>.
Alexandrov, S.A., et al, "Synthetic Aperture Fourier Holographic Optical Microscopy," Physical Review Letters, vol. 97, No. 16, Oct. 20, 2006, pp. 168102-1-168102-4. <doi: 0.1103/PhysRevLett.97.168102>.
Arimoto, H., et al, "Integral three-dimensional imaging with digital reconstruction," Optics Letters, Optical Society of America, Feb. 1, 2001, vol. 26, No. 3, pp. 157-159. <doi: 10.1364/OL.26.000157>.
Balan, R., et al, "On signal reconstruction without phase," Applied and Computational Harmonic Analysis, vol. 20, Issue 3, May 2006, pp. 345-356. <doi:10.1016/j.acha.2005.07.001>.
Balan, R., et al, "Painless Reconstruction from Magnitudes of Frame Coefficients," Journal Fourier Analysis and Applications, vol. 15, Issue 4, Mar. 25, 2009, pp. 488-501. <doi:10.1007/s00041-009-9065-1>.
Bauschke, H., et al, "Phase retrieval, error reduction algorithm, and Fienup variants: a view from convex optimization," Journal of the Optical Society America, A., vol. 19, No. 7, Jul. 2002, pp. 1334-1345. <doi: 10.1364/JOSAA.19.001334>.
Becker, S.R., et al, "Templates for Convex Cone Problems with Applications to Sparse Signal Recovery," Mathematical Programming Computation, Sep. 2010, vol. 3, No. 3, pp. 1-49. <doi: 10.1007/s12532-011-0029-5>.
Betti, R., et al, "Observational study on the mitotic rate and other prognostic factors in cutaneous primary melanoma arising from naevi and from melanoma de novo," Journal of the European Academy of Dermatology and Venereology (JEADV), Dec. 2014, vol. 28, No. 12, pp. 1738-1741. <doi: 10.1111/jdv.12395>.
Bian, L., et al, "Fourier ptychographic reconstruction using Poisson maximum likelihood and truncated Wirtinger gradient," Nature Publishing Group; Scientific Reports, vol. 6, No. 27384, Jun. 10, 2016, pp. 1-10. <doi: 10.1038/srep27384>.
Bian, L., et al, "Fourier ptychographic reconstruction using Wirtinger flow optimization," Optics Express, vol. 23, No. 4, Feb. 23, 2015, pp. 4856-4866. <doi: 10.1364/OE.23.004856>.
Bian, Z., et al, "Adaptive system correction for robust Fourier ptychographic imaging," Optics express, Dec. 30, 2013, vol. 21, No. 26, pp. 32400-32410. <doi: 10.1364/OE.21.032400>.
BioTek® Brochure: BioTek's Multi-Mode Microplate Reading Techonologies, BioTek Instruments, Inc. pp. 2. [retrieved on Mar. 14, 2016] <URL:http://www.biotek.com>.
Bishara, W., et al, "Holographic pixel super-resolution in portable lensless on-chip microscopy using a fiber-optic array," NIH-PA, Lab Chip, *Author manuscript*; available in PMC Aug. 8, 2011, pp. 1-9. (Published in final edited form as: Lab Chip. Apr. 7, 2011; 11(7): 1276-1279. <doi:10.1039/c01c00684j>).
Bishara, W., et al, "Lensfree on-chip microscopy over a wide field-of-view using pixel super-resolution," Optics Express, vol. 18, No. 11, May 24, 2010, pp. 11181-11191. <doi: 10.1364/OE.18.011181>.
Blum, A., et al, "Clear differences in hand-held dermoscopes," Journal der Deutschen Dermatologischen Gesellschaft (JDDG); Case Reports, Dec. 2006, vol. 4, No. 12, pp. 1054-1057. <doi:10.1111/j.1610-0387.2006.06128.x>.
Blum, A., et al, "Dermatoskopisch sichtbare Strukturen," Chapter 4.1 Grundlagen, Dermatoskopie von Hauttumoren: Auflichtmikroskopie; Dermoskopie; Digitale Bildanalyse; mit 28 Tabellen. Springer-Verlag Berlin Heidelberg 2003, pp. 15-66. (English Translation of Summary) <doi: 10.1007/978-3-642-57446-7_4>.
Born, M., et al, "Principles of Optics: Electromagnetic theory of propagation, interference and diffraction of light," Seventh (Expanded) Edition, Cambridge University Press, England 1999, pp. 1-31. [ISBN 0 521 642221 hardback].
Brady, D., et al, "Multiscale gigapixel photography," Nature|Letters, vol. 486, Jun. 21, 2012, pp. 386-389. <doi:10.1038/nature11150>.
Bunk, O., et al, "Influence of the overlap parameter on the convergence of the ptychographical iterative engine," Ultramicroscopy, vol. 108, (2008), pp. 481-487. <doi:10.1016/j.ultramic.2007.08.003>.
Burer, S., et al, "A nonlinear programming algorithm for solving semidefinite programs via low-rank factorization," Mathematical Programming, Series B., vol. 95, No. 2, Feb. 2003, pp. 329-357. <doi:10.1007/s10107-002-0352-8>.
Burer, S., et al, "Local Minima and Convergence in Low-Rank Semidefinite Programming," Mathematical Programming, Series A., vol. 103, Issue 3, Jul. 1, 2005, pp. 427-444. <doi:10.1007/s10107-004-0564-1>.
Candes, E.J., et al, "Phase Retrieval via Wirtinger Flow: Theory and Algorithms," IEEE Transaction on Information Theory, vol. 61, No. 4, Apr. 2015, pp. 1985-2007. <doi: 10.1109/TIT.2015.2399924>.
Candes, E.J., et al, *pre-published manuscript of* "Phase Retrieval via Matrix Completion," ArXiv e-prints, 24 pages (Submitted on Sep. 2, 2011 (v1), last revised Sep. 20, 2011 (this version, v2)). [retrieved Nov. 9, 2015] <URL: arXiv:1109.0573v2 [cs.IT] Sep. 20, 2011>.
Candes, E.J., et al, *pre-published Manuscript of* "PhaseLift: Exact and Stable Signal Recovery from Magnitude Measurements via Convex Programming," ArXiv e-prints, 31 pages (Submitted Sep. 2011 (v1)). [retrieved Nov. 9, 2015] <URL: arXiv:1109.4499v1 [cs.IT] Sep. 21, 2011>.
Carroll, J., "Adaptive Optics Retinal Imaging: Applications for Studying Retinal Degeneration," Archives of Ophthalmology, vol. 126, No. 6, Jun. 9, 2008, pp. 857-858. [retrieved Feb. 24, 2016] <doi:10.1001/archopht.126.6.857>.
Chai, A., et al, "Array imaging using intensity-only measurements," IOP Publishing: Inverse Problems, vol. 27, No. 1, Jan. 2011, pp. 1-16. <doi:10.1088/0266-5611/27/1/015005>.
Chao, W. et al, "Soft X-ray microscopy at a spatial resolution better than 15 nm," Nature|Letters, vol. 435, Jun. 30, 2005, pp. 1210-1213. <doi:10.1038/nature03719>.
Chen, T., et al, "Polarization and Phase-Shifting for 3D Scanning of Translucent Objects," 2007 IEEE Conference on Computer Vision and Pattern Recognition; on Jun. 17-22, 2007, pp. 1-8. <doi:10.1109/CVPR.2007.383209>.

(56) References Cited

OTHER PUBLICATIONS

Chin, L., et al, "Malignant melanoma: genetics and therapeutics in the genomic era," CSH Press: Genes & Development, Aug. 15, 2006, vol. 20, pp. 2149-2182. <doi: 10.1101/gad.1437206> [retrieved Sep. 9, 2015] <URL:http://genesdev.cshlp.org/content/20/16/2149>.

Choi, W., et al, "Tomographic phase microscopy," NPG: Nature Methods | Advance Online Publication, Aug. 12, 2007, pp. 1-3. <doi:10.1038/NMETH1078>.

Chung, J., et al, "Counting White Blood Cells from a Blood Smear Using Fourier Ptychographic Microscopy," PLoS ONE, vol. 10, No. 7, Jul. 17, 2015, pp. 1-10. <doi:10.1371/journal.pone.0133489>.

Chung, J., et al, "Wide field-of-view fluorescence image deconvolution with aberration-estimation from Fourier ptychography," Biomedical Optics Express, vol. 7, No. 2, Feb. 1, 2016, pp. 352-368. <doi: 10.1364/BOE.7.000352>.

Chung, J., et al, *pre-published manuscript of* "Wide-field Fourier ptychographic microscopy using laser illumination source," ArXiv e-prints (Submitted on Feb. 9, 2016 (v1), last revised Mar. 23, 2016 (this version, v2)). [retrieved on May 20, 2016] <URL:arXiv:1602.02901v2 [physics.optics] Mar. 23, 2016>.

Colomb, T., et al, "Automatic procedure for aberration compensation in digital holographic microscopy and applications to specimen shape compensation," Applied Optics, vol. 45, No. 5, Feb. 10, 2006, pp. 851-863. <doi: 10.1364/AO.45.000851>.

De Sa, C., et al, "Global Convergence of Stochastic Gradient Descent for Some Non-convex Matrix Problems," Proceedings of the 32nd International Conference on Machine Learning, Lille, France, 2015. JMLR: W&CP, vol. 37, pp. 10. [retrieved on Nov. 9, 2015]<URL: https://arxiv.org/abs/1411.1134>.

Debailleul, M., et al, "High-resolution three-dimensional tomographic diffractive microscopy of transparent inorganic and biological samples," Optics Letters, Optical Society of America, vol. 34, No. 1, Jan. 1, 2009, pp. 79-81. <doi: 10.1364/OL.34.000079>.

Denis, L., et al, "Inline hologram reconstruction with sparsity constraints," Optics Letters, Optical Society of America, vol. 34, No. 22, Oct. 12, 2009, pp. 3475-3477. <doi:10.1364/OL.34.003475> <ujm-00397994v2>.

Di, J., et al, "High resolution digital holographic microscopy with a wide field of view based on a synthetic aperture technique and use of linear CCD scanning," Applied Optics, vol. 47, No. 30, Oct. 20, 2008, pp. 5654-5659. <doi:10.1364/AO.47.005654>.

Dierolf, M., et al, "Ptychographic X-ray computed tomography at the nanoscale," Nature|Letter, vol. 467, Sep. 23, 2010, pp. 436-439. <doi:10.1038/nature09419>.

Dierolf, M., et al, "Ptychographic coherent diffractive imaging of weakly scattering specimens," New Journal of Physics, vol. 12, Mar. 31, 2010, 035017, pp. 14. <doi: 10.1088/1367-2630/12/3/035017>.

Doctor Mole—Skin Cancer App, App to check skin cancer by Dr. Mole, p. 1. (Webpage) [retrieved on Oct. 23, 2015] <URL: http://www.doctormole.com>.

Dong, S., et al, "FPscope: a field-portable high-resolution microscope using a cellphone lens," Biomedical Optics Express, vol. 5, No. 10, Oct. 1, 2014, pp. 3305-3310. <doi:10.1364/BOE.5.003305>.

Dong, S., et al, "High-resolution fluorescence imaging via pattern-illuminated Fourier ptychography," Optics Express, vol. 22, No. 17, Aug. 25, 2014, pp. 20856-20870. <doi:10.1364/OE.22.020856>.

Dong, S., et al, "Aperture-scanning Fourier ptychography for 3D refocusing and super-resolution macroscopic imaging," Optics Express, vol. 22, No. 11, Jun. 2, 2014, pp. 13586-13599. <doi:10.1364/OE.22.013586>.

Eldar, Y.C., et al, "Sparse Phase Retrieval from Short-Time Fourier Measurements," IEEE Signal Processing Letters, vol. 22, No. 5, May 2015, pp. 638-642. <doi:10.1109/LSP.2014.2364225>.

Emile, O., et al, "Rotating polarization imaging in turbid media," Optics Letters, vol. 21, No. 20, Oct. 15, 1996, pp. 1706-1708. <doi: 10.1364/OL.21.001706>.

Essen BioScience, "Real-time, quantitative live-cell analysis, IncuCyte® Zoom System," IncuCyte Zoom System Brochure 2016, pp. 1-4. [retrieved Feb. 25, 2016] [URL: http://www.essenbioscience.com/IncuCyte].

Faulkner, H.M.L., et al, "Error tolerance of an iterative phase retrieval algorithm for moveable illumination microscopy," Ultramicroscopy, vol. 103, No. 2, May 2005, pp. 153-164. <doi:10.1016/j.ultramic.2004.11.006>.

Faulkner, H.M.L., et al., "Movable Aperture Lensless Transmission Microscopy: A Novel Phase Retrieval Algorithm," Physical Review Letters, vol. 93, No. 2, Jul. 9, 2004, pp. 023903-1-023903-4. <doi:10.1103/PhysRevLett.93.023903>.

Fazel, M., "Matrix rank minimization with applications," PhD dissertation submitted to the Dept. of Electrical Engineering and Committee on Graduate Studies of Stanford University, Mar. 2002, pp. 1-117. [retrieved on Nov. 9, 2015] <URL:http://faculty.washington.edu/mfazel/thesis-final.pdf>.

Feng, P., et al, "Long-working-distance synthetic aperture Fresnel off-axis digital holography," Optics Express, vol. 17, No. 7, Mar. 30, 2009, pp. 5473-5480. <doi: 10.1364/OE.17.005473>.

Fienup, J. R., "Invariant error metrics for image reconstruction," Applied Optics, vol. 36, No. 32, Nov. 10, 1997, pp. 8352-8357. <doi: 10.1364/AO.36.008352>.

Fienup, J. R., "Lensless coherent imaging by phase retrieval with an illumination pattern constraint," Optics Express, vol. 14, No. 2, Jan. 23, 2006, pp. 498-508. <doi: 10.1364/OPEX.14.000498>.

Fienup, J. R., "Phase retrieval algorithms: a comparison," Applied Optics, vol. 21, No. 15, Aug. 1, 1982, pp. 2758-2769. <doi: 10.1364/AO.21.002758>.

Fienup, J. R., "Reconstruction of a complex-valued object from the modulus of its Fourier transform using a support constraint," Journal of the Optical Society of America A, vol. 4, No. 1, Jan. 1987, pp. 118-123. <doi:10.1364/JOSAA.4.000118>.

Fienup, J. R., "Reconstruction of an object from the modulus of its Fourier transform," Optics Letter, vol. 3, No. 1, Jul. 1978, pp. 27-29. <doi: 10.1364/OL.3.000027>.

Gan, X., et al, "Image enhancement through turbid media under a microscope by use of polarization gating methods," Journal of the Optical Society of America A, vol. 16, No. 9, Sep. 1999, pp. 2177-2184. <doi: 10.1364/JOSAA.16.002177>.

Gerke T.D., et al, "Aperiodic volume optics," Nature Photonics, vol. 4, Feb. 7, 2010, pp. 188-193. <doi:10.1038/nphoton.2009.290>.

Ghosh, A., et al, *pre-published manuscript of* "Multiview Face Capture using Polarized Spherical Gradient Illumination," via USC Institute for Creative Technologies; To appear in ACM Transactions on Graphics (TOG), vol. 30, No. 6, Dec. 2011, pp. 1-10. [Retrieved Sep. 28, 2011] <URL:http://doi.acm.org/10.1145/2024156.2024163>.

Godara, P., et al, "Adaptive Optics Retinal Imaging: Emerging Clinical Applications," *NIH-PA Author Manuscript*; available in PMC Dec. 1, 2011. Published in final edited form as: Optom. Vis. Sci.. Dec. 2010; 87(12): 930-941. <doi: 10.1097/OPX.0b013e3181ff9a8b>.

Goodman, J.W., "Introduction to Fourier Optics," Third Ed., Roberts & Company Publishers (Englewood, Colorado 2005) pp. 1-172. <ISBN 0-9747077-2-4>.

Goodson, A.G., et al, "Comparative analysis of total body vs. dermatoscopic photographic monitoring of nevi in similar patient populations at risk for cutaneous melanoma," NIH-PA *Author Manuscript*; available in PMC Jul. 1, 2011. Published in final edited form as: Dermatol. Surg. Jul. 2010; 36(7): 1087-1098. <doi:10.1111/j.1524-4725.2010.01589.x>.

Granero, L., et al, "Synthetic aperture superresolved microscopy in digital lensless Fourier holography by time and angular multiplexing of the object information," Applied Optics, vol. 49, No. 5, Feb. 10, 2010, pp. 845-857. <doi: 10.1364/AO.49.000845>.

Grant, M., et al, "CVX: Matlab Software for Disciplined Convex Programming," CVX Research Inc., pp. 1-3. [Webpage] [retrieved on Dec. 18, 2015] <URL:http://cvxr.com/cvx>.

Greenbaum, A., et al, "Field-portable wide-field microscopy of dense samples using multi-height pixel super-resolution based lensfree imaging," Lab Chip, The Royal Society of Chemistry, vol. 12, No.

(56) References Cited

OTHER PUBLICATIONS

7, Jan. 31, 2012, pp. 1242-1245. [retrieved on Feb. 27, 2016] <URL:http://dx.doi.org/10.1039/C2LC21072J>.

Greenbaum, A., et al, "Increased space-bandwidth product in pixel super-resolved lensfree on-chip microscopy," Scientific Reports, vol. 3, No. 1717, Apr. 24, 2013, pp. 1-8. [doi: 10.1038/srep01717].

Gruev, V., et al, "Dual-tier thin film polymer polarization imaging sensor," Optics Express, vol. 18, No. 18, Aug. 30, 2010, pp. 19292-19303. <doi:10.1364/OE.18.019292>.

Guizar-Sicairos, M., and Fienup, J.R.,"Phase retrieval with transverse translation diversity: a nonlinear optimization approach," Optics Express, vol. 16, No. 10, May 12, 2008, pp. 7264-7278. <doi: 10.1364/OE.16.007264>.

Gunturk, B.K., et al, "Restoration in the Presence of Unknown Spatially Varying Blur," Ch. 3, in *Image Restoration: Fundamentals and Advances* (CRC Press 2012), pp. 63-68. <ISBN 978-1-4398-6955-0>.

Guo, K., et al, "Optimization of sampling pattern and the design of Fourier ptychographic illuminator," Optics Express, vol. 23, No. 5, Mar. 9, 2015, pp. 6171-6180. <doi: 10.1364/OE.23.006171>.

Gustafsson, M.G.L., "Surpassing the lateral resolution limit by a factor of two using structured illumination microscopy," Journal of Microscopy, vol. 198, Pt. 2, May 2000, pp. 82-87. <doi:10.1046/j.1365-2818.2000.00710.x>.

Gutzler, T., et al, "Coherent aperture-synthesis, wide-field, high-resolution holographic microscopy of biological tissue," Optics Letters, vol. 35, No. 8, Apr. 15, 2010, pp. 1136-1138. <doi: 10.1364/OL.35.001136>.

Haigh, S. J., et al, "Atomic Structure Imaging beyond Conventional Resolution Limits in the Transmission Electron Microscope," Physical Review Letters, vol. 103, Issue 12, Sep. 18, 2009, pp. 126101.1-126101.4. <doi:10.1103/PhysRevLett.103.126101>.

Han, C., et al, "Wide Field-of-View On-Chip Talbot Fluorescence Microscopy for Longitudinal Cell Culture Monitoring from within the Incubator" Analytical Chemistry, vol. 85, No. 4, Jan. 28, 2013, pp. 2356-2360. <doi:10.1021/ac303356v>.

Hillman, T.R., et al, "High-resolution, wide-field object reconstruction with synthetic aperture Fourier holographic optical microscopy," Optics Express, vol. 17, No. 10, May 11, 2009, pp. 7873-7892. <doi:10.1364/OE.17.007873>.

Hofer, H., et al, "Dynamics of the eye's wave aberration," Journal of Optical Society of America A., vol. 18, No. 3, Mar. 2001, pp. 497-506. <doi: 10.1364/JOSAA.18.000497>.

Hofer, H., et al, "Organization of the Human Trichromatic Cone Mosaic," The Journal of Neuroscience, vol. 25, No. 42, Oct. 19, 2005, pp. 9669-9679. <doi: 10.1523/JNEUROSCI.2414-05.2005>.

Holloway, J., et al. "SAVI: Synthetic apertures for long-range, subdiffraction-limited visible imaging using Fourier ptychography," Science Advances | Research Article, vol. 3, No. 4, Apr. 14, 2017, pp. 1-11. <doi:10.1126/sciadv.1602564> [retrieved on Nov. 28, 2017] <URL:http://advances.sciencemag.org/>.

Hong, S-H., et al, "Three-dimensional volumetric object reconstruction using computational integral imaging," OSA Publishing: Optics Express, vol. 12, No. 3, Feb. 9, 2004, pp. 483-491. <doi:10.1364/OPEX.12.000483>.

Hoppe, W., "Diffraction in inhomogeneous primary wave fields. 1. Principle of phase determination from electron diffraction interference." Acta Crystallographica Section a-Crystal Physics Diffraction Theoretical and General Crystallography, A25, Jan. 1, 1969, pp. 495-501. (English Machine Translation Incl.).

Horstmeyer, R., et al, "A phase space model of Fourier ptychographic microscopy," Optics Express, vol. 22, No. 1, Jan. 13, 2014, pp. 338-358. <doi:10.1364/OE.22.000338>.

Horstmeyer, R., et al, "Diffraction tomography with Fourier ptychography," Optica, Optical Society of America, vol. 3, No. 8, Aug. 2016, pp. 827-835. <doi:10.1364/OPTICA.3.000827>.

Horstmeyer, R., et al, "Digital pathology with Fourier Ptychography," Computerized Medical Imaging and Graphics, vol. 42, Jun. 2015, pp. 38-43. <doi: 10.1016/j.compmedimag.2014.11.005>.

Horstmeyer, R., et al, "Overlapped Fourier coding for optical aberration removal," Optics Express, vol. 22, No. 20, Oct. 6, 2014, pp. 24062-24080. <doi: 10.1364/OE.22.024062>.

Horstmeyer, R., et al, "Solving ptychography with a convex relaxation," New Journal of Physics, vol. 17, May 27, 2015, pp. 1-14. <doi: 10.1088/1367-2630/17/5/053044> [URL: http://iopscience.iop.org/1367-2630/17/5/053044].

Horstmeyer, R., et al, "Standardizing the resolution claims for coherent microscopy," Nature Photonics | Commentary, vol. 10, No. 2, Feb. 2016, pp. 68-71. <doi:10.1038/nphoton.2015.279> [URL: http://dx.doi.org/10.1038/nphoton.2015.279].

Hüe, F., et al, "Wave-front phase retrieval in transmission electron microscopy via ptychography," Rapid Comunications: Physical Review B, vol. 82, No. 12, Sep. 15, 2010, pp. 121415-1-121415-4. <doi:10.1103/PhysRevB.82.121415>.

Humphry, M., et al, "Ptychographic electron microscopy using high-angle dark-field scattering for sub-nanometre resolution imaging," Nature Communications, vol. 3, Mar. 6, 2012, pp. 1-7. <doi: 10.1038/ncomms1733>.

Jaganathan, K., et al, "Recovery of sparse 1-D signals from the magnitudes of their Fourier transform," *2012 IEEE International Symposium on Information Theory Proceedings*, Cambridge, MA, 2012, pp. 1473-1477. <doi: 10.1109/ISIT.2012.6283508.>.

Jaganathan, K., et al, "Phase retrieval with masks using convex optimization," 2015 IEEE International Symposium on Information Theory (ISIT), Hong Kong, 2015, pp. 1655-1659. <doi: 10.1109/ISIT.2015.7282737>.

Jaganathan, K., et al, *pre-published manuscript of* "STFT Phase retrieval: uniqueness guarantees and recovery algorithms," ArXiv e-prints, 10 pages, (Submitted on Aug. 12, 2015 (v1). <doi: 10.1109/JSTSP.2016.2549507> [retrieved Nov. 9, 2015] <URL: https://arxiv.org/abs/1508.02820v1>.

Joeres, S., et al, "Retinal Imaging With Adaptive Optics Scanning Laser Ophthalmoscopy in Unexplained Central Ring Scotoma," Arch. Ophthalmol., vol. 126, No. 4, Apr. 2008, pp. 543-547. [retrieved Jun. 10, 2015] [URL: http://archopht.jamanetwork.com/].

Jung, J.H., et al, *Author Manuscript of* "Microfluidic-integrated laser-controlled microactuators with on-chip microscopy imaging functionality," Published in final edited form as: Lab Chip, Oct. 7, 2014, vol. 14, No. 19, pp. 3781-3789. <doi:10.1039/c41c00790e>.

Kawata, S. et al, "Optical microscope tomography. I. Support constraint," Journal Optical Society America A, vol. 4, No. 1, Jan. 1987, pp. 292-297. <doi:10.1364/JOSAA.4.000292>.

Kay, D. B., et al, *Author Manuscript of* "Outer Retinal Structure in Best Vitelliform Macular Dystrophy," Published in final edited form as: JAMA Ophthalmol., Sep. 2013, vol. 131, No. 9, pp. 1207-1215. <doi: 10.1001/jamaophthalmol.2013.387>.

Kim, J., et al, "Incubator embedded cell culture imaging system (EmSight) based on Fourier ptychographic microscopy," Biomedical Optics Express, vol. 7, No. 8, Aug. 1, 2016, pp. 3097-3110. <doi: 10.1364/BOE.7.003097>.

Kim, M., et al, "High-speed synthetic aperture microscopy for live cell imaging," Optics Letters, vol. 36, No. 2, Jan. 15, 2011, pp. 148-150. <doi:10.1364/OL.36.000148>.

Kim, M., et al, "High-speed synthetic aperture microscopy for live cell imaging," NIH-PA, *Author Manuscript* available in PMC Mar. 30, 2011. Published in final edited form as: Opt Lett. Jan. 15, 2011; 36(2): pp. 148-150. <PMCID: PMC3068016>.

Kirkland, A.I., et al, "Multiple beam tilt microscopy for super resolved imaging," Journal of Electron Microscopy (Tokyo) Jan. 1, 1997, vol. 46, No. 1, pp. 11-22. [doi: 10.1093/oxfordjournals.jmicro.a023486].

Kirkland, A.I., et al, "Super-resolution by aperture synthesis: tilt series reconstruction in CTEM," Elsevier Science B.V., Ultramicroscopy 57, Mar. 1995, pp. 355-374. <doi:10.1016/0304-3991(94)00191-O>.

Kittler, H., et al, "Morphologic changes of pigmented skin lesions: A useful extension of the ABCD rule for dermatoscopy," Journal of the American Academy of Dermatology (JAAD), Apr. 1999. vol. 40, No. 4, pp. 558-562. <doi: 10.1016/S0190-9622(99)70437-8>.

Kner, P., "Phase diversity for three-dimensional imaging," Journal of the Optical Society of America A, vol. 30, No. 10, Oct. 1, 2013, pp. 1980-1987. <doi:10.1364/JOSAA.30.001980>.

(56) References Cited

OTHER PUBLICATIONS

Kozak, I., "Retinal imaging using adaptive optics technology," Saudi Journal of Ophthalmology, vol. 28, No. 2, Feb. 25, 2014, pp. 117-122. <doi:10.1016/j.sjopt.2014.02.005>.

Lauer, V., "New Approach to optical diffraction tomography yielding a vector equation of diffraction tomography and a novel tomographic microscope," Journal of Microscopy, Feb. 2002, vol. 205, No. 2, pp. 165-176. <doi: 10.1046/j.0022-2720.2001.00980.x>.

Lee, K., et al, "Synthetic Fourier transform light scattering," Optics Express, vol. 21, No. 19, Sep. 23, 2013, pp. 22453-22463. <doi:10.1364/OE.21.022453>.

Levoy, M., et al, "Light field microscopy," ACM Transactions Graphics, vol. 25, No. 3, proceedings of ACM SIGGRAPH Jul. 2006, pp. 1-11. [doi: 10.1145/1141911.1141976].

Levoy, M., et al, "Recording and controlling the 4D light field in a microscope using microlens arrays," Journal of Microscopy, vol. 235, Pt. 2, Aug. 2009, pp. 144-162. <doi:10.1111/j.1365-2818.2009.03195.x>.

Li, X., et al, "Sparse Signal Recovery from Quadratic Measurements via Convex Programming," SIAM Journal on Mathematical Analysis, vol. 45, No. 5, Sep. 26, 2013, pp. 3019-3033. [doi:10.1137/120893707] [retrieved Feb. 13, 2014] <URL: http://dx.doi.org/10.1137/120893707>.

Lohmann, A. W., et al, "Space-bandwidth product of optical signals and systems," Journal of the Optical Society of America A, vol. 13, No. 3, Mar. 1996, pp. 470-473. <doi: 10.1364/JOSAA.13.000470>.

Lu, H., et al, "Quantitative phase imaging and complex field reconstruction by pupil modulation differential phase contrast," Optics Express, vol. 24, No. 22, Oct. 31, 2016, pp. 25345-25361. <doi:10.1364/OE.24.025345>.

Lue, N., et al, "Live Cell Refractometry Using Hilbert Phase Microscopy and Confocal Reflectance Microscopy," NIH-PA *Author Manuscript*, available in PMC Apr. 22, 2010. Published in final edited form as: J Phys Chem A. Nov. 26, 2009; 113(47); 13327-13330. <PMCID: PMC2858636>.

Luxexcel® Brochure, "Luxexcel: 3D Printing Service Description" pp. 1-5. [retrieved on Mar. 7, 2016] <URL: http://www.luxexcel.com>.

Lytro | Illum, Lytro-Products [webpages], pp. 1-6. [Online] [retrieved Oct. 23, 2015] <URL:https://www.lytro.com/>.

Ma, W., et al, "Rapid Acquisition of Specular and Diffuse Normal Maps from Polarized Spherical Gradient Illumination," EGSR'07 Proceedings of the 18th Eurographics conference on Rendering Techniques, Eurographics Association, Aire-la-Ville, Switzerland 2007, pp. 183-194. <doi: 10.2312/EGWR/EGSR07/183-194>.

Mahajan, V. N., "Zernike Circle Polynomials and Optical Aberrations of Systems with Circular Pupils," Engineering Laboratory Notes: Supplemental to *Applied Optics*, vol. 33 No. 34, Dec. 1, 1994, pp. 8121-8124. <doi: 10.1364/AO.33.008121>.

Maiden, A. M., et al, "A new method of high resolution, quantitative phase scanning microscopy," in Proceedings of SPIE, Jun. 2, 2010, vol. 7729, pp. 77291I-1-77291I-8. <doi: 10.1117/12.853339> [retrieved on Dec. 16, 2015] <URL: proceedings.spiedigitallibrary.org>.

Maiden, A. M., et al, "An improved ptychographical phase retrieval algorithm for diffractive imaging," Ultramicroscopy, vol. 109, No. 10, Sep. 2009, pp. 1256-1262. <doi:10.1016/j.ultramic.2009.05.012>.

Maiden, A. M., et al, "Superresolution imaging via ptychography," Journal of the Optical Society of America A. (JOSAA), vol. 28, No. 4, Apr. 1, 2011, pp. 604-612. <doi: 10.1364/JOSAA.28.000604>.

Maiden, A. M., et al, "Optical ptychography: a practical implementation with useful resolution," Optics Letters, vol. 35, No. 15, Aug. 1, 2010, pp. 2585-2587. <doi: 10.1364/OL.35.002585>.

Marchesini S., "Invited Article: A unified evaluation of iterative projection algorithms for phase retrieval," Review of Scientific Instruments, vol. 78, No. 1, Apr. 19, 2007, pp. 011301-1-011301-10. <doi: 10.1063/1.2403783> [retrieved May 7, 2014] <URL: http://dx.doi.org/10.1063/1.2403783>.

Marchesini S., et al, *pre-published manuscript of* "Augmented projections for ptychographic imaging," (Submitted on Sep. 21, 2012 (v1), last revised Aug. 29, 2013 (this version, v5)) pp. 1-18. Published in Inverse Problems vol. 29, No. 11 (2013). [retrieved on Nov. 9, 2015] <URL: https://arxiv.org/pdf/1209.4924>.

Marrison, J., et al, "Ptychography—a label free, high-contrast imaging technique for live cells using quantitative phase information," Scientific Reports, vol. 3, No. 2369, Aug. 6, 2013, pp. 1-7. <doi: 10.1038/srep02369>.

Medoff, B.P., et al, "Iterative convolution backprojection algorithms for image reconstruction from limited data," Journal of the Optical Society of America, vol. 73, No. 11, Nov. 1, 1983, pp. 1493-1500. <doi: 10.1364/JOSA.73.001493>.

Melafind, Optics by Carl Zeiss, MELA Sciences 2015, pp. 1-4. [Webpage] [retrieved Oct. 23, 2015] <URL: http://www.melafind.com/>.

Meyer, R.R., et al, "A new method for the determination of the wave aberration function of high-resolution TEM. 2. Measurement of the antisymmetric aberrations," Ultramicroscopy, vol. 99, No. 2-3, May 2004, pp. 115-123. <doi: 10.1016/j.ultramic.2003.11.001>.

Miao, J., et al, "High Resolution 3D X-Ray Diffraction Microscopy," Physical Review Letters, vol. 89, No. 8, Aug. 19, 2002, pp. 088303-1-088303-4. <doi: 10.1103/PhysRevLett.89.088303>.

Mico, V., et al, "Synthetic aperture microscopy using off-axis illumination and polarization coding," Optics Communications, vol. 276, No. 2, Aug. 15, 2007, pp. 209-217. <doi:10.1016/j.optcom.2007.04.020>.

Mico, V., et al, "Synthetic aperture superresolution with multiple off-axis holograms," Journal of the Optical Society of America A, vol. 23, No. 12, Dec. 1, 2006, pp. 3162-3170. <doi:10.1364/JOSAA.23.003162>.

Mir, M. et al, "Optical measurement of cycle-dependent cell growth," Proceedings of the National Academy of Sciences (PNAS) vol. 108, No. 32, Aug. 9, 2011, pp. 13124-13129. <doi:10.1073/pnas.1100506108>.

Mir, M., et al, "Blood screening using diffraction phase cytometry," Journal of Biomedical Optics: vol. 15, No. 2, Mar./Apr. 2010, pp. 027016-1-027014-4. <doi:10.1117/1.3369965> [retrieved on Feb. 6, 2015] <URL:http://dx.doi.org/10.1117/1.3369965>.

Moreno, I., "Creating a desired lighting pattern with an LED array," Proceedings of SPIE, Eighth International Conference on Solid State Lighting, vol. 705811, Sep. 2, 2008, pp. 9. <doi:10.1117/12.795673>.

Mrejen, S., et al, "Adaptive Optics Imaging of Cone Mosaic Abnormalities in Acute Macular Neuroretinopathy," Ophthalmic Surgery, Lasers & Imaging Retina, vol. 45, No. 6, Nov./Dec. 2014, pp. 562-569. <doi: 10.3928/23258160-20141118-12>.

Nayar, S. K., et al, *pre-published manuscript of* "Fast separation of direct and global components of a scene using high frequency illumination," (Submitted 2006, this one (v.1)), Published in: ACM SIGGRAPH 2006 Papers, Boston, Massachusetts Jul.-Aug. 3, 2006, pp. 935-944. <doi: http://dx.doi.org/10.1145/1179352.1141977>.

Ng, R., et al, "Light Field Photography with a Hand-held Plenoptic Camera," Stanford Tech Report, Computer Science Technical Report (CSTR) Apr. 20, 2005, vol. 2, No. 11, pp. 1-11. <URL: https://classes.soe.ucsc.edu/cmps290b/Fall05/readings/lfcamera-150dpi.pdf>.

Nomura, H., et al., "Techniques for measuring aberrations in lenses used in photolithography with printed patterns," Applied Optics, vol. 38, No. 13, May 1, 1999, pp. 2800-2807. <doi: 10.1364/AO.38.002800>.

Ohlsson, H., et al, "Compressive Phase Retrieval From Squared Output Measurements Via Semidefinite Programming," arXiv:1111.6323, Technical Report; Nov. 28, 2011, pp. 6. <URL: http://cds.cern.ch/record/1402765>.

Ou, X., et al, "High numerical aperture Fourier ptychography: principle, implementation and characterization," Optics Express, vol. 23, No. 3, Feb. 9, 2015, pp. 3472-3491. <doi: 10.1364/oe.23.003472>.

Ou, X., et al, "Aperture scanning Fourier ptychographic microscopy," Biomedical Optics Express, vol. 7, No. 8, Aug. 1, 2016, pp. 3140-3150. <doi:10.1364/BOE.7.003140>.

Ou, X., et al, "Quantitative phase imaging via Fourier ptychographic microscopy," NIH-PA *Author Manuscript*; available in PMC Dec.

(56) References Cited

OTHER PUBLICATIONS 26, 2014. Published in final edited form as: Opt Lett. Nov. 15, 2013; 38(22): 4845-4848. <doi: 10.1364/OL.38.004845>.

Ou. X., et al, "Embedded pupil function recovery for Fourier ptychographic microscopy," Optics Express, vol. 22, No. 5, Mar. 10, 2014, pp. 4960-4972. <doi:10.1364/OE.22.004960> *Erratum Attached-*, dated Dec. 28, 2015, vol. 23, No. 26, p. 33027. <doi:10.1364/OE.23.033027>.

Ou. X., et al, *pre-published manuscript of* "Embedded pupil function recovery for Fourier ptychographic microscopy," (submitted on Dec. 26, 2013 (this version, v1); revised Feb. 12, 2014; accepted Feb. 17, 2014; published Feb. 24, 2014) pp. 1-13. <doi:10.1364/OE.22.004960>.

Pacheco, S., et al, "Reflective Fourier Ptychography," Journal of Biomedical Optics, vol. 21, No. 2, Feb. 18, 2016, pp. 026010-1-026010-7. <doi: 10.1117/1.JBO.21.2.026010> [retrieved on Mar. 8, 2016] <URL: http://biomedicaloptics.spiedigitallibrary.org>.

Phillips, Z., et al, "Multi-Contrast Imaging and Digital Refocusing on a Mobile Microscope with a Domed LED Array," PLoS One, vol. 10, No. 5, May 13, 2015, pp. 1-13. <doi:10.1371/journal.pone.0124938>.

Recht, B., et al, "Guaranteed Minimum-Rank Solutions of Linear Matrix Equations via Nuclear Norm Minimization," SIAM Review, vol. 52, No. 3, Aug. 5, 2010, pp. 471-501. <doi: 10.1137/070697835> [retrieved on Nov. 20, 2015] <URL: https://doi.org/10.1137/070697835>.

Reinhard, E., et al, "High Dynamic Range Imaging: Acquisition, Display, and Image-based Lighting" Second Edition § 5.2 HDR Image Capture: Morgan Kaufmann, May 28, 2010, pp. 148-151. <ISBN: 9780123749147>.

Rodenburg, J. M., et al, "A phase retrieval algorithm for shifting illumination," Applied Physics Letters, vol. 85, No. 20, Nov. 15, 2004, pp. 4795-4797. <doi: 10.1063/1.1823034>.

Rodenburg, J. M., et al, "Hard-X-ray Lensless Imaging of Extended Objects," Physical Review Letters, vol. 98, No. 3, Jan. 19, 2007, pp. 034801-1-034801-4. <doi: 10.1103/PhysRevLett.98.034801>.

Rodenburg, J. M., et al, "The Theory of Super-Resolution Electron Microscopy Via Wigner-Distribution Deconvolution," Philosophical Transactions of the Royal Society A, vol. 339, No. 1655, Jun. 15, 1992, pp. 521-553. <doi:10.1098/rsta.1992.0050>.

Rodenburg, J.M., "Ptychography and related Diffractive Imaging Methods," Adv. Imaging Electron Phys., vol. 150, Dec. 31, 2008, pp. 87-184. <doi:10.1016/S1076-5670(07)00003-1>.

Rossi, E.A., et al, "In vivo imaging of retinal pigment epithelium cells in age related macular degeneration," Biomedical Optics Express, vol. 4, No. 11, Nov. 1, 2013, pp. 2527-2539. <doi: 10./1364/BOE.4.002527].

Rowe, M., et al, "Polarization-difference imaging: a biologically inspired technique for observation through scattering media," Optics Letters, vol. 20, No. 6, Mar. 15, 1995, pp. 608-610. <doi:10.1364/OL.20.000608>.

Sankaranarayanan, Aswin C., et al, "CS-MUVI: Video Compressive Sensing for Spatial-Multiplexing Cameras," Proceedings of the IEEE International Conference Computational Photography (ICCP), Apr. 2012, pp. 11. <doi:10.1109/ICCPhot.2012.6215212>.

Schechner, Y., "Multiplexing for Optimal Lighting," IEEE Transactions on Pattern Analysis and Machine Intelligence, vol. 29, No. 8, Aug. 2007, pp. 1339-1354. <doi:10.1109/TPAMI.2007.1151.>.

Schnars, U., et al, "Digital recording and numerical reconstruction of holograms," Measurement Science and Technology, vol. 13, No. 9, Aug. 7, 2002, pp. R85-R101. <doi: 10.1088/0957-0233/13/9/201>.

Schwarz, C., et al, "Imaging interferometric microscopy," Optics letters, vol. 28, No. 16, Aug. 15, 2003, pp. 1424-1426. <doi: 10.1364/OL.28.001424>.

Shechner, Y., et al, "Polarization-based vision through haze," Applied Optics, vol. 42, No. 3, Jan. 20, 2003, pp. 511-525. <doi: 10.1364/AO.42.000511>.

Shechtman, Y., et al, "Sparsity based sub-wavelength imaging with partially incoherent light via quadratic compressed sensing," Optics Express, vol. 19, No. 16, Aug. 1, 2011, pp. 14807-14822. <doi:10.1364/OE.19.014807>.

Siegel, R., et al, "Cancer Statistics 2013," CA: A Cancer Journal for Clinicians, vol. 63, No. 1, Jan. 1, 2013, pp. 11-30. <doi:10.3322/caac.21166>.

Stoecker, W., et al, "Diagnostic Inaccuracy of Smartphone Applications for Melanoma Detection: Representative Lesion Sets and the Role for Adjunctive Technologies," JAMA Dermatology, vol. 149, No. 7, Jul. 1, 2013, pp. 884-884. <doi:10.1001/jamadermatol.2013.4334>.

Sun, D., et al, "Estimating a signal from a magnitude spectrogram via convex optimization," arXiv preprint arXiv:1209.2076, Sep. 10, 2012, pp. 1-7. [retrieved Nov. 9, 2015] <URL: https://arxiv.org/abs/1209.2076>.

Sun, J., "Coded multi-angular illumination for Fourier ptychography based on Hadamard codes," In Proc. SPIE, vol. 9524, Jul. 17, 2015, pp. 95242C-1-94242C-5. <doi:10.1117/12.2189655> [retrieved Jul. 23, 2015] <URL: http://proceedings.spiedigitallibrary.org>.

Tam, K., et al, "Tomographical imaging with limited-angle input," Journal of the Optical Society of America, vol. 71, No. 5, May 1981, pp. 582-592. <doi:doi.org/10.1364/JOSA.71.000582>.

Thibault, P. et al, "Probe retrieval in ptychographic coherent diffractive imaging," Ultramicroscopy, vol. 109, No. 4, Mar. 2009, pp. 338-343. <doi:10.1016/j.ultramic.2008.12.011>.

Thibault, P., et al, "High-resolution scanning X-ray diffraction microscopy," Science AAAS, vol. 321, No. 5887, Jul. 18, 2008, pp. 379-382. <doi:10.1126/science.1158573>.

Thomas, L., et al, "Semiological Value of ABCDE Criteria in the Diagnosis of Cutaneous Pigmented Tumors," Dermatology, vol. 197, No. 1, Jul. 13, 1998, p. 11-17. <doi:10.1159/000017969>.

Tian, L., et al, "3D differential phase-contrast microscopy with computational illumination using an LED array," Optics Letters, vol. 39, No. 5, Mar. 1, 2014, pp. 1326-1329. <doi:10.1364/OL39.001326>.

Tian, L., et al, "Computational illumination for high-speed in vitro Fourier ptychographic microscropy," Optica: Research Article, vol. 2, No. 10, Oct. 14, 2015, pp. 904-911. <doi:10.1364/OPTICA.2.000904>.

Tian, L., et al, "Multiplexed Coded Illumination for Fourier Ptychography with an LED Array Microscope," Biomedical Optics Express, vol. 5, No. 7, Jul. 1, 2014, pp. 14. <doi:10.1364/BOE.5.002376>.

Tippie, A.E., et al, "High-resolution synthetic-aperture digital holography with digital phase and pupil correction," Optics Express, vol. 19, No. 13, Jun. 20, 2011, pp. 12027-12038. <doi:10.1364/OE.19.012027>.

Turpin, T., et al, "Theory of the synthetic aperture microscope," SPIE Proceedings, vol. 2566: Advanced Imaging Technologies and Commercial Applications, Aug. 23, 1995, pp. 230-240. [retrieved Mar. 16, 2015] <URL: http://dx.doi.org/10.1117/12.217378>.

Tyson, R., "Principles of Adaptive Optics" Third Ed., Series in Optics and Optoelectronics, CRC Press, Sep. 14, 2010, pp. 1-299. <ISBN: 13: 978-1-4398-0859-7>.

Vulovic, M., et al, "When to use the projection assumption and the weak-phase object approximation in phase contrast cryo-EM," Ultramicroscopy, vol. 136, Jan. 2014, pp. 61-66.<doi:10.1016/j.ultramic.2013.08.002>.

Waldspurger, I., et al, "Phase recovery, MaxCut and complex semidefinite programming," Mathematical Programming, vol. 149, No. 1-2, Feb. 2015, pp. 47-81. <doi:10.1007/s10107-013-0738-9>.

Wang, Q., et al, "Adaptive Optics Microperimetry and OCT Images Show Preserved Function and Recovery of Cone Visibility in Macular Telangiectasia Type 2 Retinal Lesions," Investigative Ophthalmology Visual Science, vol. 56, No. 2, Feb. 2015, pp. 778-786. <doi:10.1167/iovs.14-15576> [retrieved on Apr. 5, 2016] [URL: http://iovs.arvojournals.org].

Wang, Z., et al, "Tissue refractive index as marker of disease," Journal of Biomedical Optics, vol. 16, No. 11, Nov. 2011, pp. 116017-1-16017-7. <doi:10.1117/1.3656732>.

(56) References Cited

OTHER PUBLICATIONS

Watanabe, M., et al, "Telecentric optics for focus analysis," IEEE Transactions on Pattern Analysis and Machine Intelligence: Short Papers, vol. 19, No. 12, Dec. 1997, pp. 1360-1365. <doi:10.1109/34.643894>.
Wesner, J., et al, "Reconstructing the pupil function of microscope objectives from the intensity PSF," Proc. SPIE 4767, Current Developments in Lens Design and Optical Engineering III, 32 (Oct. 1, 2002), pp. 32-43. <doi:10.1117/12.451320> [retrieved Dec. 16, 2015] <URL:http://proceedings.spiedigitallibrary.org>.
Williams, A., et al, "Fourier ptychographic microscopy for filtration-based circulating tumor cell enumeration and analysis," Journal of Biomedical Optics, vol. 19, No. 6, Jun. 20, 2014, pp. 066007.1-66007.8. <doi:10.1117/1.JBO.19.6.066007> [retrieved Feb. 10, 2016] <URL:http://biomedicaloptics.spiedigitallibrary.org>.
Wills, S., "Synthetic Apertures for the Optical Domain," Optics & Photonics News Article [webpage], The Optical Society (OSA), Apr. 18, 2017, pp. 2. <URL:https://www.osa-opn.org/home/newsroom/2017/april/synthetic_apertures_for_the_optical_domain/>.
Wolf, J., et al, "Diagnostic Inaccuracy of Smartphone Applications for Melanoma Detection," JAMA Dermatol. *Author Manuscript*; available in PMC May 13, 2014. Published in final edited form as: JAMA Dermatol. Apr. 2013; 149(4): 422-426. <doi:10.1001/jamadermatol.2013.2382>.
Wu, J., et al, "Focal plane tuning in wide-field-of-view microscope with Talbot pattern illumination," Optics Letters, vol. 36, No. 12, Jun. 15, 2011, pp. 2179-2181. <doi: 145985>.
Wu, J., et al, "Harmonically matched grating-based full-field quantitative high-resolution phase microscope for observing dynamics of transparent biological samples," Optics Express, vol. 15, No. 26, Dec. 24, 2007, pp. 18141-18155. <doi:10.1364/OE.15.018141>.
Wu, J., et al, "Paired-angle-rotation scanning optical coherence tomography forward-imaging probe," Optics Letters, vol. 31, No. 9, May 1, 2006, pp. 1265-1267. <doi:10.1364/OL.31.001265>.
Wu, J., et al, "Wide field-of-view microscope based on holographic focus grid illumination," Optics Letters, vol. 35, No. 13, Jul. 1, 2010, pp. 2188-2190. <doi:10.1364/OL.35.002188>.
Xu, W., et al, "Digital in-line holography for biological applications," Proceedings of the National Academy of Sciences of the USA (PNAS), vol. 98, No. 20, Sep. 25, 2001, pp. 11301-11305. <doi:10.1073/pnas.191361398>.
Yeh, et al., "Experimental robustness of Fourier ptychography phase retrieval algorithms," Optics Express, vol. 23, No. 26, Dec. 28, 2015, pp. 33214-33240. <doi: 10.1364/OE.23.033214>.
Yuan, C., et al, "Angular multiplexing in pulsed digital holography for aperture synthesis," Optics Letters, vol. 33, No. 20, Oct. 15, 2008, pp. 2356-2358. <doi:10.1364/OL.33.002356>.
Zeiss, C., "Microscopy: Cells Need the Perfect Climate. System Solutions for Live Cell Imaging under Physiological Conditions," ZEISS Product Brochure, Carl Zeiss Microscopy GmbH Co., Feb. 2008, pp. 42. <URL: http://www.zeiss.de/incubation>.
Zhang, Y., et al, "Self-learning based Fourier ptychographic microscopy," Optics Express, vol. 23, No. 14, Jul. 13, 2015, pp. 18471-18486. <doi: 10.1364/OE.23.018471>.
Zhang, Y., et al, "Photoreceptor perturbation around subretinal drusenoid deposits as revealed by adaptive optics scanning laser ophthalmoscopy," HHS Public Access, Am J Ophthalmol. *Author Manuscript*, Sep. 1, 2015, pp. 22. (Published in final edited form as: Am J Ophthalmol. Sep. 2014; 158(3): 584-96.e1.).
Zheng, G. "The ePetri dish, an on-chip cell imaging platform based on subpixel perspective sweeping microscopy (SPSM)," PNAS Early Edition, Published online before print Oct. 3, 2011, pp. 6. <doi:10.1073/pnas.1110681108>.
Zheng, G., "Fourier Ptychographic Imaging: A MATLAB tutorial," IOP Concise Physics, Morgan & Claypool Publication, San Rafael, CA., May 2016, pp. 96. <ISBN: 978-1-6817-4272-4 (ebook)> <doi: 10.1088/978-1-6817-4273-1>.
Zheng, G., et al, "Characterization of spatially varying aberrations for wide field-of-view microscopy," Optics Express, vol. 21, No. 13, Jul. 1, 2013, pp. 15131-15143. <doi:10.1364/OE.21.015131>.

Zheng, G., et al, "Microscopy refocusing and dark-field imaging by using a simple LED array," Optics Letters, vol. 36, No. 20, Oct. 15, 2011, pp. 3987-3989. <doi: 10.1364/OL.36.003987>.
Zheng, G., et al, "Wide-field, high-resolution Fourier ptychographic microscopy," Nature Photonics, vol. 7, Sep. 2013, Published Online Jul. 28, 2013, pp. 739-746. <doi:10.1038/NPHOTON.2013.187>.
Zheng, G., et al, "0.5 gigapixel microscopy using a flatbed scanner," Biomedical Optics Express, vol. 5, No. 1, Jan. 1, 2014, pp. 1-8. <doi: 10.1364/BOE.5.000001>.
Zheng, G., et al, "Sub-pixel resolving optofluidic microscope for on-chip cell imaging," Lab Chip, vol. 10, Sep. 29, 2010, pp. 3125-3129. <doi:10.1039/c0Lc00213e> [retrieved on Oct. 4, 2010] <URL: http://pubs.rsc.org>.
Zheng, G., et al, "Wide-field, high-resolution Fourier ptychographic microscopy," HHS Public Access, *Nat. Photonics. Author Manuscript*;available in PMC Sep. 19, 2014, pp. 1-16. (Published in final edited form as: Nat Photonics. Sep. 1, 2013; 7(9): 739-745. <doi:10.1038/nphoton.2013.187>).
U.S. Appl. No. 15/820,295, filed Nov. 21, 2017, Ou.
Preliminary Amendment dated Jun. 13, 2018 filed in U.S. Appl. No. 15/820,295.
U.S. Final Office Action dated Nov. 29, 2018 in U.S. Appl. No. 14/065,280.
U.S. Office Action dated Dec. 26, 2018 in U.S. Appl. No. 15/963,966.
U.S. Office Action dated Dec. 26, 2018 in U.S. Appl. No. 15/959,050.
U.S. Notice of Allowance dated Sep. 17, 2018 in U.S. Appl. No. 15/820,295.
U.S. Office Action dated Oct. 4, 2018 in U.S. Appl. No. 14/658,019.
U.S. Notice of Allowance dated Jul. 25, 2018 in U.S. Appl. No. 14/710,947.
U.S. Office Action dated Dec. 13, 2018 in U.S. Appl. No. 14/960,252.
U.S. Notice of Allowance dated Jun. 27, 2018 in U.S. Appl. No. 15/636,494.
U.S. Notice of Allowance dated Oct. 5, 2018 in U.S. Appl. No. 15/636,494.
U.S. Notice of Allowance dated Jul. 16, 2018 in U.S. Appl. No. 15/007,159.
U.S. Office Action dated Sep. 7, 2018 in U.S. Appl. No. 14/979,154.
U.S. Office Action dated Apr. 4, 2018 issued in U.S. Appl. No. 15/003,559.
U.S. Final Office Action dated Dec. 10, 2018 issued in U.S. Appl. No. 15/003,559.
U.S. Office Action Interview Summary dated May 3, 2018 in U.S. Appl. No. 15/068,389.
U.S. Final Office Action dated Jun. 6, 2018 issued in U.S. Appl. No. 15/068,389.
U.S. Notice of Allowance dated Feb. 9, 2018 in U.S. Appl. No. 15/081,659.
U.S. Office Action dated Apr. 13, 2018 issued in U.S. Appl. No. 15/160,941.
U.S. Notice of Allowance dated Oct. 19, 2018 issued in U.S. Appl. No. 15/160,941.
Japanese First Office Action dated Jul. 31, 2018 issued in Application No. JP 2016-531919.
European Extended Search Report dated Jun. 6, 2018 issued in Application No. 15865492.1.
Extended European Search Report dated Aug. 8, 2018 issued in Application No. EP 16744002.3.
Chinese First Office Action dated Feb. 24, 2018 issued in CN 201680003937.1.
European Extended Search Report dated Aug. 14, 2018 issued in EP 16744003.1.
Extended European Search Report dated Jul. 3, 2018 issued in Application No. EP 15874344.3.
Extended European Search Report dated Sep. 12, 2018 issued in Application No. EP 16740769.1.
Chinese Second Office Action dated Jul. 3, 2018 issued in Application No. CN 201480054301.0.
Extended European Search Report dated Oct. 25, 2018 issued in Application No. EP 16765505.9.
Chinese Third Office Action dated Jul. 13, 2018 issued in CN 201480057911.6.

(56) References Cited

OTHER PUBLICATIONS

Australian Examination Report No. 1, dated Jan. 18, 2018 issued in AU 2014308673.
Godden, T.M. et al., "Ptychographic microscope for three-dimensional imaging," Optics Express, vol. 22, No. 10, May 19, 2014, pp. 12513-12523.
Jacques, et al., "Imaging Superficial Tissues With Polarized Light," Lasers in Surgery and Medicine, vol. 26, No. 2, Apr. 25, 2000, pp. 119-129.
Jensen, et al. "Types of imaging, Part 2: An Overview of Fluorescence Microscopy." The Anatomical Record, vol. 295, No. 10, Oct. 1, 2012, pp. 1621-1627.
Maiden, A.M., et al., "Ptychographic transmission microscopy in three dimensions using a multi-slice approach," Journal of the Optical Society of America A., vol. 29, No. 8, Aug. 1, 2012, pp. 1606-1614.
Sarder, et al. "Deconvolution Methods for 3-D Fluorescence Microscopy Images," IEEE Signal Processing Magazine, vol. 23, No. 3, May 2006, pp. 32-45.
U.S. Appl. No. 16/162,271, filed Oct. 16, 2018, Kim et al.
U.S. Appl. No. 16/171,270, filed Oct. 25, 2018, Horstmeyer et al.
U.S. Appl. No. 16/179,688, filed Nov. 2, 2018, Chan et al.
U.S. Appl. No. 16/242,934, filed Jan. 8, 2019, Kim et al.
U.S. Notice of Allowance dated Apr. 16, 2019 in U.S. Appl. No. 15/820,295.
U.S. Office Action dated Apr. 4, 2019 in U.S. Appl. No. 16/162,271.
U.S. Notice of Allowance dated Jan. 14, 2019 in U.S. Appl. No. 15/820,295.
U.S. Office Action dated Mar. 8, 2019 in U.S. Appl. No. 16/171,270.
U.S. Office Action dated Jan. 17, 2019 issued in U.S. Appl. No. 15/068,389.
Chinese First Office Action dated Jan. 28, 2019 issued in CN 201580072950.8.
Chinese First Office Action dated Dec. 28, 2018 issued in Application No. CN 201680005491.6.
Chinese First Office Action dated Dec. 26, 2018 issued in Application No. CN 201580067354.0.
International Search Report and Written Opinion dated Feb. 22, 2019 issued in PCT/US2018/059059.
Pankajakshan, P., "Blind Deconvolution for Confocal Laser Scanning Microscopy," Doctoral dissertation, Universite Nice Sophia Antipolis, 2009. <URL: https://tel.archives-ouvertes.fr/tel-00474264>.
U.S. Appl. No. 16/252,465, filed Jan. 18, 2019, Ou et al.
U.S. Office Action dated Jun. 26, 2019 issued in U.S. Appl. No. 14/065,280.
U.S. Notice of Allowance dated Apr. 19, 2019 in U.S. Appl. No. 15/963,966.
U.S. Final Office Action dated Jun. 3, 2019 in U.S. Appl. No. 15/959,050.
U.S. Final Office Action dated May 30, 2019 in U.S. Appl. No. 14/658,019.
U.S. Final Office Action dated May 30, 2019 in U.S. Appl. No. 14/979,154.
U.S. Office Action dated Jun. 26, 2019 in U.S. Appl. No. 15/003,559.
U.S. Final Office Action dated Jun. 19, 2019 issued in U.S. Appl. No. 15/068,389.
Chinese First Office Action dated Apr. 19, 2019 issued in Application No. CN 201680006738.6.
Chinese First Office Action dated Apr. 19, 2019 issued in Application No. CN 201680014898.5.
Soulez, et al., "Blind deconvolution of 3D data in wide field fluorescence microscopy" In 2012 9th IEEE International Symposium on Biomedical Imaging (ISBI) May 2, 2012, pp. 1735-1738.
U.S. Notice of Allowance dated Aug. 12, 2019 in U.S. Appl. 14/960,252.
Adie, et al., "Computational adaptive optics for broadband optical interferometric tomography of biological tissue," Proc. Natl. Acad. Sci. USA 109, 7175-7180 (May 8, 2012).
Bian, et al., "Content adaptive illumination for Fourier ptychography," Opt. Lett. 39, 6648-6651 (Aug. 2014).
Bioucas-Dias, et al., "Total variation-based image deconvolution: a majorization-minimization approach," ICASSP (2), pp. 861-864 (May 14, 2006).
Booth, "Adaptive optical microscopy: the ongoing quest for a perfect image," Light Sci. Appl. 3, e165 (Apr. 25, 2014 ).
Chung, et al., "Computational aberration compensation by coded-aperture-based correction of aberration obtained from optical Fourier coding and blur estimation," Optica 6, 647-661 (May 10, 2019).
Dowski, et al., "Extended depth of field through wavefront coding," Appl. Opt. 34, 1859-1866 (Apr. 10, 1995).
Evered, et al., "Accuracy and perceptions of virtual microscopy compared with glass slide microscopy in cervical cytology," Cytopathology, vol. 22, Feb. 2, 2010, pp. 82-87.
Fergus, et al., "Removing camera shake from a single photograph," ACM Trans. Graph. 25, 787-794 (2006).
Fienup and Miller, "Aberration correction by maximizing generalized sharpness metrics," J. Opt. Soc. Am. A 20, pp. 609-620 (Apr. 2003).
Fried, D.L.,"Anisoplanatism in adaptive optics," J. Opt. Soc. Am. 72, pp. 52-61 (Jan. 1982).
G. Gunjala, S. Sherwin, A. Shanker, and L. Waller, "Aberration recovery by imaging a weak diffuser," Opt. Express 26, 21054-21068 (Aug. 6, 2018).
G. McConnell, J. Trägårdh, R. Amor, J. Dempster, E. Reid, and W. B. Amos, "A novel optical microscope for imaging large embryos and tissue volumes with sub-cellular resolution throughout," eLife 5, e18659 (Sep. 23, 2016).
G. Muyo and A. R. Harvey, "Wavefront coding for athermalization of infrared imaging systems," Proc. SPIE 5612, 227-235 (Dec. 2004).
G. Muyo, A. Singh, M. Andersson, D. Huckridge, A. Wood, and A. R. Harvey, "Infrared imaging with a wavefront-coded singlet lens," Opt. Express 17, 21118-21123 (Nov. 5, 2009).
Ginner, et al., "Holographic line field en-face OCT with digital adaptive optics in the retina in vivo," Biomed. Opt. Express 9, 472-485 (Feb. 1, 2018).
Ginner, et al., "Noniterative digital aberration correction for cellular resolution retinal optical coherence tomography in vivo," Optica, vol. 4, Aug. 1, 2017, pp. 924-931.
Gustafsson, M.,"Nonlinear structured-illumination microscopy: widefield fluorescence imaging with theoretically unlimited resolution," Proc. Natl. Acad. Sci. USA 102, 13081-13086 (Sep. 13, 2005).
H. Hofer, L. Chen, G. Y. Yoon, B. Singer, Y. Yamauchi, and D. R. Williams, "Improvement in retinal image quality with dynamic correction of the eye's aberrations," Opt. Express 8, 631-643 (May 21, 2001).
Hillmann, et al., "Aberration-free volumetric high-speed imaging of in vivo retina," Sci. Rep. 6, 35209 (Oct. 20, 2016).
Kamal, et al., "In situ retrieval and correction of aberrations in moldless lenses using Fourier ptychography," Opt. Express, vol. 26, No. 3, pp. 2708-2719 (Feb. 5, 2018).
Kuang, et al., "Digital micromirror device-based laserillumination Fourier ptychographic microscopy," Opt. Express 23, 26999-27010 (Oct. 5, 2015).
Kubala, et al., "Reducing complexity in computational imaging systems," Opt. Express 11, 2102-2108 (Sep. 8, 2003).
Kumar, et al., "Subaperture correlation based digital adaptive optics for full field optical coherence tomography," Opt. Express, vol. 21, May 6, 2013, pp. 10850-10866.
Kundur, et al., "Blind Image Deconvolution," IEEE Signal Process. Mag. 13(3), pp. 43-64 (May 1996).
Levin et al., "Image and depth from a conventional camera with a coded aperture," ACM Trans. Graph. 26, 70 (Jul. 2007).
Levin, et al., "Understanding blind deconvolution algorithms," IEEE Trans. Pattern Anal. Mach. Intell. 33, 2354-2367 (Dec. 2011 ).
Li, et al., "Separation of threedimensional scattering effects in tilt-series Fourier ptychography," Ultramicroscopy 158, 1-7 (Jun. 14, 2015).
Marcos, et al., "Vision science and adaptive optics, the state of the field," Vis. Res. 132, 3-33 (Feb. 27, 2017).

(56) References Cited

OTHER PUBLICATIONS

Martins da Silva et al., "Photosensitivity and epilepsy: current concepts and perspectives—a narrative review," Seizure 50, 209-218 (Apr. 4, 2017).
Neumaier, "Solving ill-conditioned and singular linear systems: a tutorial on regularization," SIAM Rev. 40, 636-666 (1998).
Pan, et al., "Subwavelength resolution Fourier ptychography with hemispherical digital condensers," Opt. Express 26, 23119-23131 (Sep. 3, 2018).
Pan, et al., "System calibration method for Fourier ptychographic microscopy," J. Biomed. Opt. 22, 096005 (Sep. 12, 2017).
Pan, et al., "Three-dimensional space optimization for near-field ptychography," Opt. Express 27, 5433-5446 (Feb. 18, 2019).
Qian, et al., "Large-scale 3D imaging of insects with natural color," Opt. Express 27, 4845-4857 (Feb. 18, 2019).
Reinig, et al., "Adaptative optics microscopy enhances image quality in deep layers of CLARITY processed brains of YFP-H mice" Proc., of SPIE, vol. 9690, (Mar. 9, 2016), pp. 969008-1-969008-12. <doi:10.1117/12.2213283>.
Rha, et al., "Adaptive optics flood-illumination camera for high speed retinal imaging," Opt. Express 14, 4552-4569 (May 15, 2006).
Shemonski, et al., "Computational high-resolution optical imaging of the living human retina," Nat. Photonics 9, 440-443 (Jul. 2015).
Sun, et al., "Efficient positional misalignment correction method for Fourier ptychographic microscopy," Biomed. Opt. Express 7, 1336-1350 (Mar. 17, 2016).
Sun, et al., "Resolution-enhanced Fourier ptychographic microscopy based on high-numerical-aperture illuminations," Sci. Rep. 7, 1187 (Apr. 26, 2017).
Sun, et al., "Sampling criteria for Fourier ptychographic microscopy in object space and frequency space," Opt. Express 24, 15765-15781 (Jul. 11, 2016).
Thiébaut and Conan, "Strict a priori constraints for maximumlikelihood blind deconvolution," J. Opt. Soc. Am. A 12, 485-492 (Mar. 1995).
Tian and Waller, "3D intensity and phase imaging from light field measurements in an LED array microscope," Optica 2, 104-111 (Jan. 28, 2015).
Tomer et al., "Advanced CLARITY for rapid and high-resolution imaging of intact tissues," Nat. Protoc., vol. 9, No. 7, Jul. 2014, pp. 1682-1697.
Wade, et al., "A fast, robust pattern recognition system for low light level image registration and its application to retinal imaging," Opt. Express 3, 190-197 (Aug. 31, 1998).
Williams, D., "Imaging Single Cells in the Living Retina," Vis. Res. 51, pp. 1379-1396 (Jul. 1, 2011).
Yaroslaysky, L., "Theoretical Foundations of Digital Imaging Using MATLAB" (CRC Press, Nov. 26, 2012).
Yuan, et al., "Image deblurring with blurred/noisy image pairs," ACM Trans. Graph. 26, 1 (Jul. 29, 2007).
Zhou, et al., "What are good apertures for defocus deblurring?" in 2009 IEEE International Conference on Computational Photography (IEEE, Apr. 16-17, 2009), pp. 1-8.
U.S. Appl. No. 16/552,948, filed Aug. 27, 2019, Chung et al.
US Ex Parte Quayle Action dated Aug. 8, 2019 issued in U.S. Appl. No. 16/242,934.
U.S. Notice of Allowance dated Nov. 4, 2019 issued in U.S. Appl. No. 16/242,934.
U.S. Office Action dated Sep. 23, 2019 issued in U.S. Appl. No. 16/252,465.
U.S. Office Action dated Oct. 11, 2019 issued in U.S. Appl. No. 16/179,688.
U.S. Notice of Allowance dated Nov. 20, 2019 in U.S. Appl. No. 15/959,050.
U.S. Notice of Allowance dated Dec. 9, 2019 in U.S. Appl. No. 16/162,271.
Chinese Second Office Action dated Nov. 12, 2019 issued in Application No. CN 201680005491.6.
Chinese Second Office Action dated Nov. 28, 2019 issued in Application No. CN 201680006738.6.

* cited by examiner

PUPIL PTYCHOGRAPHY METHODS AND SYSTEMS

CROSS-REFERENCES TO RELATED APPLICATIONS

This application claims priority to U.S. Provisional Patent Application No. 62/348,433, titled "Characterizing the Aberration of an Optical System with Spatially Incoherent Light Using Pupil Ptychography" and filed on Jun. 10, 2016, which is hereby incorporated by reference in its entirety and for all purposes.

FEDERALLY SPONSORED RESEARCH OR DEVELOPMENT

This invention was made with government support under Grant No. EY026228 awarded by the National Institutes of Health. The government has certain rights in the invention.

FIELD

Certain embodiments described herein are generally related to digital imaging, and more specifically to pupil ptychography (PP) imaging methods and systems which may be implemented, for example, to characterize aberration of an optical system using spatially incoherent illumination.

BACKGROUND

High-resolution retinal imaging can significantly improve the quality of diagnosis, disease progression tracking and assessment of therapy in a broad range of retinal diseases including, for example, retinal degenerations (retinitis pigmentosa), macular telangiectasis, macular dystrophies, age-related macular degeneration (AMD), and inflammatory diseases. Some of these diseases are prevalent (AMD afflicts 12% of the population aged 80+, and retinitis pigmentosa is the most common cause of blindness/low-vision in adults 20-60 years old) and progress slowly, which drives the need for a cost-effective imaging solution that can be broadly deployed for screening and tracking purposes. The availability of new therapeutics further drives this need for a cost-effective imaging solution since the ability to discern the exact impact of the drugs at the cell level is highly useful in informing clinicians about the course of treatments.

Accounting for the numerical aperture of the eye as set by a nominal pupil diameter of 6 mm, an imaging system should be able to focus light to a diffraction-limited spot of size of 1.9 microns on the retina (630 nm wavelength) except that aberrations in the eye actually result in a much poorer focus spot. Conventional retinal imaging techniques correct for aberrations by including a corrective physical optical arrangement to compensate for the aberrations before acquiring images. This conventional strategy is the basis of the adaptive optics (AO) work that was first started in astronomy and that has been applied to ophthalmic imaging systems, in particular confocal scanning laser ophthalmoscopes (cSLO). Conventional adaptive optics scanning laser ophthalmoscopes (AOSLO) have significant limitations that have hindered their broad clinical use. First, the field of view of AO corrected images tends to be very small oftentimes only 1 degree in size. Since retinal diseases can occupy large portions of the macula and retina, conventional AO techniques requires multiple images to be obtained and montaged and increases the acquisition time. Long acquisition times are generally impractical for routine clinical use, especially with eye motion from the patient. This requires high-speed tracking systems since AO requires feedback to keep the aberration correction current. Second, the uneven topology of many retinal diseases presents a major challenge because regions not in the focal plane of the optics will appear out of focus. Third, despite reductions in the cost of certain components, such as deformable mirrors, these conventional systems still remain expensive, limiting their commercial feasibility.

Fourier ptychography is a resolution-enhancement imaging technique that can be applied to a conventional 4f optical arrangement to increase the system's effective numerical aperture, remove the inherent optical aberrations in the system, and allow for quantitative phase measurement of a sample. Details of the Fourier ptychography imaging technique are described in G. Zheng, R. Horstmeyer and C. Yang, "Wide-field, high-resolution Fourier ptychographic microscopy," Nature Photonics, 2013, which is hereby incorporated by reference in its entirety. Fourier ptychography typically uses the aberration characterization technique referred to as the Embedded Pupil Function Recovery (EPRY) method, which is described in X. Ou, G. Zheng and C. Yang, "Embedded pupil function recovery for Fourier ptychographic microscopy," Optics Express, 2014, which is hereby incorporated by reference in its entirety. The EPRY method is based on images acquired using coherent illumination, such as from light-emitting diodes (LEDs) placed sufficiently far away from the sample or a collimated laser beam, to provide coherent illumination with a consistent beam profile to the sample at varied illumination angles sequentially (i.e. at different sample times). The EPRY method uses the sequence of images captured when the sample is illuminated by various angles with coherent illumination to reconstruct the system's aberration function, also known as the pupil function, while simultaneously reconstructing the sample's complex function. However, it is difficult to deliver a consistent illumination beam at varied illumination angles to a sample if the path between the coherent illumination source and the sample is under the influence of unknown refraction effects. For example, if one were to image the retinal surface of a human eye in-vivo, the coherent illumination needs to be provided via the cornea, lens, and the vitreous humor inside the eye before reaching the retinal surface. Because it is very hard to know the exact refractive error caused by these elements, the illumination profile reaching the retinal surface is not usually known and the EPRY technique cannot usually be applied directly to reconstruct the pupil function of the eye without some error introduced. In another example, EPRY cannot usually be applied directly to characterize the aberrations of a digital camera when taking pictures of natural scenes because it is not practical to deliver coherent illumination at varied angles to natural scenes being imaged.

SUMMARY

Certain embodiments pertain to pupil ptychography (also referred to herein as "PP") techniques that use spatially incoherent illumination to characterize aberration in an optical system.

Certain embodiments pertain to a pupil ptychography system comprises an aperture modulator configured to modulate apertures at the Fourier plane of a first imager. The first imager is configured to acquire a full pupil image of the sample being incoherently illuminated during operation, and configured to acquire a sequence of N limited-aperture images of the sample while the aperture modulator modulates a first aperture to N locations at the Fourier plane of the first imager. The pupil ptychography system further comprises optical components configured to propagate light reflected from the sample to the aperture modulator and propagate light from the aperture modulator to the first imager. The pupil ptychography system further comprises at least one processor configured to use the N limited-aperture images to recover a pupil function of an optical system in an optical path between the sample and the first imager and deconvolve the full pupil image of the sample using the recovered pupil function to generate a substantially aberration-free full pupil image of the sample.

Certain embodiments pertain to a pupil ptychography method that comprises receiving, from a first imager, a sequence of N limited-aperture images of a sample being incoherently illuminated, the N limited-aperture images being acquired while the aperture modulator sequentially generates a first aperture at N different locations at the Fourier plane of the first imager. The method further comprises receiving a full pupil image of the sample, recovering a pupil function of an optical system in an optical path between the sample and the first imager the sequence of N limited-aperture images, and deconvolving the full pupil image of the sample using the recovered pupil function to generate a substantially aberration-free full pupil image of the sample.

These and other features are described in more detail below with reference to the associated drawings.

DETAILED DESCRIPTION

Figure 1:
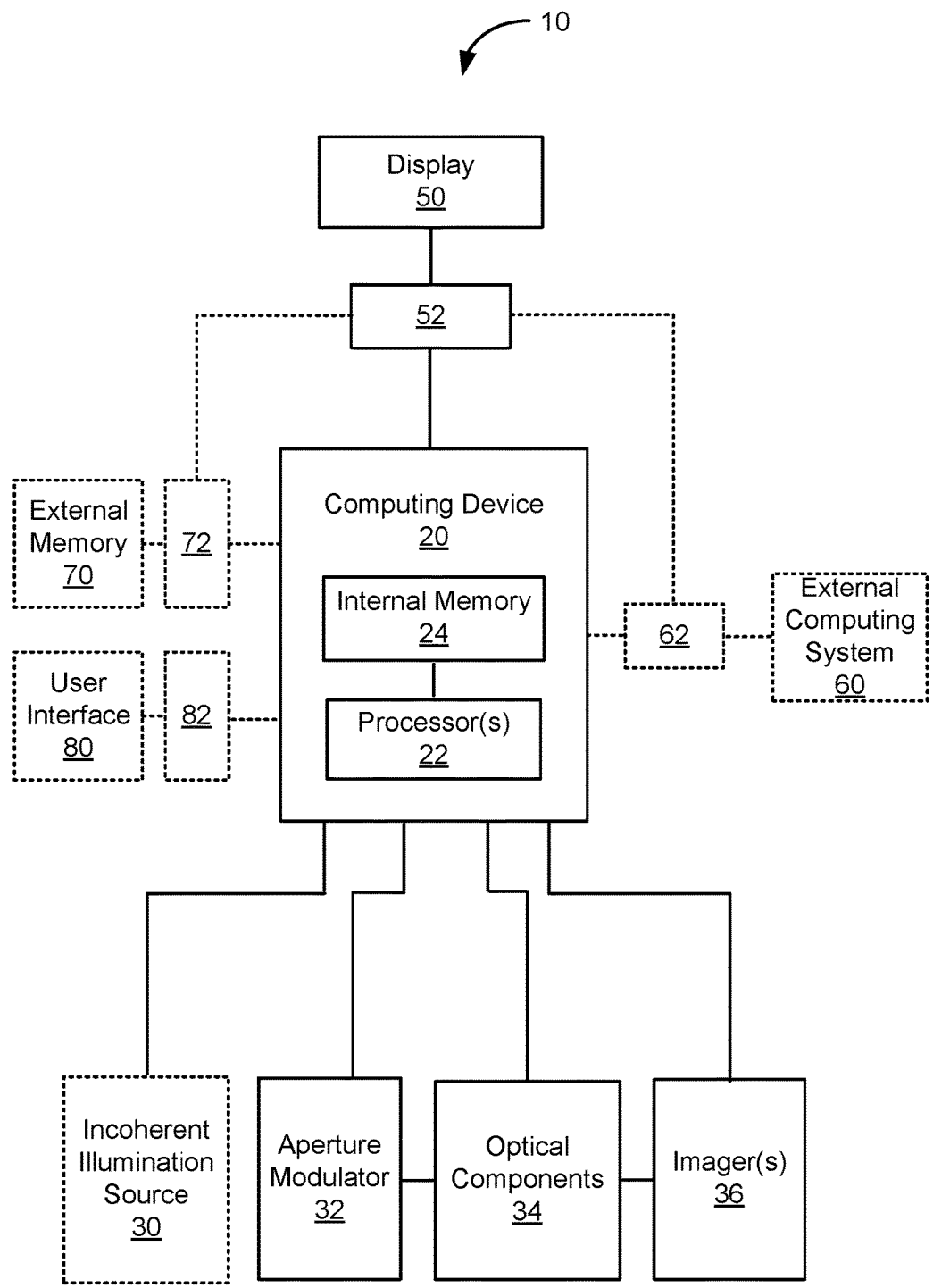
FIG. 1 illustrates a simplified block diagram of a pupil ptychography imaging system, according to various implementations.

Embodiments pertain to pupil ptychography techniques that can be used to characterize aberration of an optical system using monochromatic, spatially-incoherent illumination. Pupil ptychography techniques can use the reconstructed aberration to deconvolve from an image captured with the optical system to remove the aberration to generate an image that is aberration-free or substantially free of aberration. Pupil ptychography techniques can be implemented, for example, in retinal imaging or imaging of natural scenes.

Generally speaking, pupil ptychography techniques capture a series of N limited-aperture images and a full aperture image of a sample of interest that is illuminated by monochromatic, spatially-incoherent illumination, computationally determine the aberration of the optical system, and deconvolve the full aperture image to remove the aberration. In the case of a moving sample, unmodulated images are also captured in parallel with the N limited-aperture images to be able to correct for the sample's motion. When used to image a wide field-of-view, the aberration of the optical system and, by extension, the pupil function can be expected to show spatial variations and the aberration may not be the same for different regions within the field-of-view. In this case, the entire field-of view of each of the captured images is segmented into smaller tiles (also referred to herein as "tile images"). Within each tile, the aberration can be assumed to be constant and the aberration characterization procedure is applied to each tile. The pupil ptychography techniques use either one of the limited-aperture images, or a slightly expanded limited aperture image, as ground-truth. The ground truth image is then used to deconvolve all the limited-aperture images to recover a point-spread function (PSF) associated with each limited aperture. These PSFs of the limited aperture images are the intensity information of the various low-pass filtered versions of the actual complex PSF of the system with the full aperture opened. The pupil ptychography techniques use a phase retrieval process to synthesize these low-pass PSFs into the full-sized complex pupil function. An example of a phase retrieval process that can be used is described with respect to the flowchart shown in FIG. 6. After reconstructing the complex pupil function, the PSF associated with the complex pupil function can be easily calculated, which can then be used to deconvolve from the full-aperture image to obtain an aberration-removed image of the sample of interest. Because deconvolution can be sensitive to noise and suffer from the PSFs having zeros inside their passband, a robust deconvolution process can be used and/or multiple images taken to reduce the artifacts resulting from deconvolution according to certain implementations.

As used herein, an "optical system" generally refers to any entities in the optical path between the sample being imaged and the imaging sensor. In a retinal imaging example, the optical system includes the portions of the eye between the retina being imaged and the outer surface of the lens, and the optical components between the eye and the imaging sensor. The pupil ptychography imaging systems and methods described herein are configured to determine aberration of this optical system.

In various implementations, the pupil ptychography imaging system comprises an aperture modulator, optical components, and at least one imager. In implementations with a non-moving sample, the pupil ptychography imaging system comprises an aperture modulator, optical components, and an imager configured to acquire a sequence of N limited-aperture images of a sample being imaged, a full aperture image of the sample with the entire pupil region open, and optionally a slightly larger than limited-aperture image i.e. one based on a slightly larger pupil region than the limited aperture images. If the sample is moving, a second imager (with unmodulated pupil i.e. full aperture) is implemented to keep track of the motion of the sample. In implementations with a moving sample, the pupil ptychography imaging system comprises an aperture modulator, optical components, a first imager, and a second imager. The first imager is configured to acquire a sequence of N limited-aperture images of the moving sample, a full aperture image of the sample with the entire pupil region open, and optionally a slightly larger than limited-aperture image i.e. one based on a slightly larger pupil region than the limited aperture images. The second imager is configured to acquire unmodulated images of the moving sample in parallel with the first imager capturing images of the sample to account for relative movement of the sample for any of the images that the first imager is acquiring.

In some implementations such as retinal imaging, the pupil ptychography imaging system further comprises an illumination source which provides incoherent illumination to the surface of interest being imaged. In other implementations, such as an implementation for imaging natural scenes, incoherent illumination is provided by ambient light or a separate component. The optical components are configured to propagate light reflected from the sample to the aperture modulator, and from the aperture modulator to a first imager. In the case of a moving sample, the optical components also propagate light from the sample directly to a second imager.

In the case of a non-moving sample implementation, the first imager and the aperture modulator are synced so that the first imager captures one of the sequence of N limited-aperture images at the same time as the aperture modulator provides an aperture at one of the N different locations at the Fourier plane of the first imager. The same procedure applies to the full aperture and slightly-bigger-limited-aperture images, with the first imager synchronized to capture an image when the aperture modulator, e.g., SLM, displays the associated aperture. In the case of a moving sample implementation, the first imager, the second imager, and the aperture modulator are synced so that the first imager capture a limited aperture image and the second imager capture an unmodulated image at the same time as the aperture modulator provides an aperture at one of the N different locations at the Fourier plane of the first imager. For example, the aperture modulator may be an SLM that displays an aperture on the first imager's Fourier plane for each image capture. Depending on the optical system being measured, these intensity measurements taken by the imager(s) can have long durations or performed quickly for cases such as retinal imaging of an in-vivo eye. In the case of retinal imaging of an in-vivo eye or other moving samples, the images captured at different sample times may have relative spatial shifts with respect to one another due to the sample's movement. These shifts can be correctly registered by using the second imager's images since these images are not modulated in any way other than by the movement. This motion registration is an important operation implemented prior to characterizing the aberration of the optical system since the lateral shift in the captured images may incorrectly encode aberration information in the reconstruction process. The pupil ptychography imaging system also includes one or more processors for executing instructions for implementing the pupil ptychography imaging method described with respect to FIGS. 5 and 6 to reconstruct the pupil function of the optical system and an aberration-removed image of the surface of interest.

Some embodiments of the pupil ptychography methods and systems may provide one or more technical advantages. For example, certain embodiments can correct for the optical distortions of the eye or a poor camera lens (since images of natural scenes are generally taken with cameras) image acquisition which provides a simpler (simpler to use and simpler optics) and less expensive scheme than conventional methods. In addition, pupil ptychography methods and systems use spatially incoherent illumination, which is immune to speckle noise. In addition, since the pupil ptychography methods and systems perform aberration correction post-acquisition, the pupil ptychography method is robust since the aberration correction process and image acquisition process are separated. Aberration correction can be done and the image rendering can be finessed at a later time after image acquisition, without imposing additional time during the acquisition process. One advantage to pupil ptychography techniques is that aberration correction can be done after image acquisition. This can be an advantage over conventional retinal imaging, for example, which require that aberration be corrected during image acquisition which extends examination time which could become uncomfortable for a patient. Also, certain embodiments of the pupil ptychography methods and systems can be used to refocus the corrected image after image acquisition, which also allows for the ability to generate a topological profile of the sample. The refocusing can be done digitally by deconvolving the captured full-aperture sample image with the associated defocus and finding the plane with the sharpest contrast in the image. The location of such plane represents the topological height of that region; doing this for multiple regions in the retina can generate the topological map of the retina.

II. Pupil Ptychography Imaging Systems

FIG. 1 illustrates a simplified block diagram of a pupil ptychography imaging system 10, according to various implementations. The pupil ptychography imaging system 10 comprises a computing device 20 with one or more processors 22 and an internal memory 24 in electrical communication with the one or more processors 22. The pupil ptychography imaging system 10 further comprises an aperture modulator 32, optical components 34, and at least one imager 36. In implementations with a non-moving sample, the pupil ptychography imaging system 10 implements a first imager. In implementations with a moving sample, the pupil ptychography imaging system 10 further implements a second imager for tracking motion of the moving sample. As denoted by solid lines between the illustrated optical components 34, the optical components 34 are configured to propagate light reflected from the sample being imaged to the aperture modulator 32 and from the aperture modulator 32 to a first imager of the imagers 36. In an implementation for a moving sample, the optical components 34 are further configured to propagate light reflected from the sample to a second imager of the imagers 36. The second imager is configured to acquire unmodulated images of the moving sample in parallel with the first imager capturing images of the sample to account for relative movement of the sample for any of the images that the first imager is acquiring.

The pupil ptychography imaging 10 further comprises a communication interface 52 and a display 50 in communication with the communication interface 52. The computing device 20 is configured or configurable to output raw data, processed data such as image data, and/or other data over the communication interface 52 for display on the display 50. Optionally (denoted by dashed lines), the pupil ptychography imaging 10 may further comprise one or more of a communication interface 62 and an external computing device 60 in communication with the communication interface 62, a communication interface 72 and an external memory device 70 in communication with the communication interface 72 for optional storage of data to the external memory device 70, and a communication interface 82 in communication with a user interface 80 for receiving input from an operator of the system 10. The optional user interface 80 is in electrical communication with the computing device 20 through the communication interface 82 to be able to send a control signal to the computing device 20 based on input received at the user interface.

As used herein, an aperture modulator generally refers to a device, such as a spatial light modulator (also referred to herein as an "SLM"), that can selectively block (or transmit) the light field and reflect light from an aperture region at a surface or alternatively block the light field and transmit light from the aperture region. In various embodiments, the aperture modulator is configured to generate transmissive or reflective apertures (in some cases with different sizes) at different times at various locations along a surface at the Fourier (pupil) plane of the first imager. For example, a first aperture may be located at a position $x_1$, $y_1$ at time $t_1$ and a second aperture may be located at a position $x_2$, $y_2$ at time $t_2$. The locations of the modulated apertures and the exposure times of the first imager can be synchronized so that the first imager can take a sequence of N limited aperture images based on the N different locations of the modulated apertures at the Fourier plane. For example, the aperture modulator may modulate an aperture with a first size at a first location during the exposure time needed to capture a first, limited aperture image, and then modulate an aperture with the first size at a second location during the exposure time needed to capture a second, limited aperture image, and so on until a sequence of N limited aperture images based on apertures having the first size has been captured. The aperture modulator also modulates an aperture equivalent to the desired system numerical aperture (NA) during an exposure time needed to capture a full aperture image.

In FIG. 1, the aperture modulator 32 is configured to modulate apertures having a first size sequentially to N different locations at a surface placed at the Fourier plane of the first imager of the imagers 36. While the apertures having the first size are modulated sequentially to N different locations, the first imager acquires a sequence of N limited-aperture images (i.e. limited by the aperture of the first size) of the sample. Optionally, the aperture modulator 32 may also be configured to modulate an aperture of a second size to the surface at the Fourier plane of the first imager of the imagers 36 at another sample time. In this implementation, while the aperture having the second size is modulated to the Fourier plane, the first imager acquires a limited aperture image based on the second size. Some examples of a first size of an aperture that may be used include 10%, 20%, and 30% of the optical system's numerical aperture (NA). The second size may be larger than the first size, for example, at least 5% larger, at least 10% larger or at least 15% larger.

According to various implementations, a pupil ptychography imaging system includes at least one imager configured to be activated during various exposure (sample) times to capture images of the sample during an image acquisition cycle. In implementations with a moving sample, the pupil ptychography imaging system implements a first imager and a second imager for tracking motion. The pupil ptychography imaging system 10 shown in FIG. 1 includes a first imager for capturing limited aperture images and a full aperture image. Optionally, the pupil ptychography imaging system 10 may further implement a second imager for capturing unmodulated images used to track relative motion of the sample. In one implementation, the pupil ptychography imaging system 10 may comprise both the first imager and second imager and then only use the unmodulated images taken by the second imager for motion correction or may only capture unmodulated images by the second imager if it is determined that that the sample is moving.

The limited aperture images captured by the first imager are based on apertures modulated at a surface at the Fourier plane of the first imager by the aperture modulator 32. The first imager is generally configured to capture a sequence of N limited-aperture images (also referred herein as "a series of N limited-aperture images") and a full aperture image. The second imager is generally configured to capture a series of unmodulated-aperture images in parallel with the first imager for the correction of the sample's motion. A "limited aperture image" generally refers to an image acquired by the first imager based on a limited pupil function, which is a portion of the full pupil function of the optical system. The limited pupil function is defined by the aperture size at the Fourier plane as modulated by the aperture modulator. The aperture size corresponds to a spatial frequency range of the complex image. The image data of each limited aperture image includes intensity information of a low-pass filtered version of the full aperture image and the intensity information of the low-pass filtered version of the full aperture pupil function. A "full aperture image" (also referred to herein as "full pupil image") refers to an image acquired by the first imager based on the full pupil function of the optical system of the pupil ptychography imaging system. The full aperture image is captured while the aperture modulator displays an aperture equivalent to the desired system NA. An "unmodulated image" refers to an image acquired by the second imager that is not modulated by the aperture modulator. The "unmodulated image" is modulated only by spatial shifts of the moving sample. The parallel sequence of unmodulated-aperture images is used for image registration of first imager's images for motion correction.

In some implementations, the first imager is configured to capture limited-aperture images based on different apertures sizes. For example, the first imager may capture a sequence of N limited-aperture images based on a first aperture size, capture a slightly larger limited-aperture image based on a second aperture size that is slightly larger than the first aperture size, and capture a full aperture image. The slightly larger limited-aperture image has a slightly larger frequency range. For example, the second aperture may have an aperture size that is one of 5%, 10%, or 15% larger than the first aperture size.

During a general operation of the pupil ptychography imaging system 10, a sample being imaged is illuminated by monochromatic, spatially-incoherent light. Light reflected from the surface(s) of the sample is collected to the aperture modulator 32 by the optical components 34. If the sample is moving, the pupil ptychography imaging system 10 has a second imager and the optical components 34 are further configured to propagate light reflected from the surface(s) of the sample to the second imager of the imagers 36. During an image acquisition cycle, the computing device 20 sends one or more signals to the aperture modulator 32 and the first imager to synchronize the exposure times for capturing the sequence of N limited aperture images with the aperture modulator 32 modulating apertures (also called windows) at N different locations at the Fourier plane of the first imager. The computing device 20 also sends one or more signals to the aperture modulator 32 and the first imager to synchronize the exposure time for capturing a full aperture image while the aperture modulator 32 displays an aperture equivalent to the desired system NA. The desired system NA may be determined by the maximum, or close to the maximum NA of the optical system. This is defined by the f number in the case of a camera lens, and by the focal length and the pupil size of the eye in the case of an in vivo eye. In one implementation for imaging a moving sample, the computing device 20 also sends one or more signals to the second imager to synchronize the exposure times with the first imager so that the second imager captures unmodulated images of the sample for motion registration. Optionally, the aperture modulator 32 also modulates a second aperture at the Fourier plane of a first imager where the second aperture is larger than the first aperture and the first imager captures a limited aperture image based on the larger aperture size. The processor(s) 22 receives one or more signals with the image data from the images captured by the imager(s) 36. The processor(s) 22 executes instructions to perform functions of the pupil ptychography imaging method. For a wide field-of-view imaging, the processor(s) 22 performs a tiling procedure which segments the field-of view of the captured images into smaller tiles (also referred to herein as "tile images") within which the aberration is assumed to be constant. The processor(s) 22 recovers the pupil function of the optical system given the spatially incoherent images in an aberration characterization procedure. For a wide field-of-view, this procedure recovers a pupil function for each tile region. During the aberration characterization procedure, a phase retrieval process is used to synthesize the intensity information of the low-passed point spread functions (PSFs) of the N limited aperture images into a full-sized complex pupil function of the optical system. The point spread function of the optical system can be calculated from the complex pupil function. In a deconvolving procedure, the processor(s) 22 deconvolve the full aperture image to generate a substantially aberration free or aberration free complex image of the sample. For a wide field-of-view image, the deconvolving procedure deconvolves each of the tile images to generate aberration-free or substantially aberration free tile images and then combines (mosaics) together the images to form a full field of view image.

Generally, pupil ptychography imaging systems described herein are configured to acquire a sequence of N limited-aperture images of a sample, a full aperture image with the entire pupil region open, and optionally an image with a slightly larger aperture than the N limited-aperture images. In the case of a moving sample, the pupil ptychography imaging system is further configured to acquire a parallel sequence unmodulated-pupil images. Each pupil ptychography imaging system comprises an aperture modulator, optical components, and at least one imager. In some cases, the pupil ptychography imaging systems also include an illumination source which provides monochromatic, spatially-incoherent illumination to the surface of the sample being imaged. In other cases, such as an implementation used to image natural scenes, incoherent illumination can be provided by ambient sunlight or an illumination source separate from the system.

In implementations that include an illumination source, the illumination source is configured to provide monochromatic, spatially incoherent illumination to the surface of the sample. In one aspect, the illumination source is configured to generate monochromatic, spatially-incoherent illumination. An example of such a monochromatic, spatially-incoherent illumination source includes a diffuse laser emitting diode (LED) or a superluminescent diode (SLD). In one particular implementation, the illumination source comprises one or more extended LEDs or SLDs coupled to a multimode optical fiber for directing the illumination to the sample being imaged. The LED/SLD is also in electrical communication with a power source or in electrical communication with a computing device that controls power to the LED/SLD. The LED/SLD may be triggered to be switched on only for the duration of the camera's exposure window to reduce the sample's exposure to light. As an example, a fiber coupled LED (e.g. M530F2 from Thorlabs) with an LED driver (DC2200 from Thorlabs) allow for externally triggered illumination. In another implementation, the illumination source is configured to generate monochromatic, coherent illumination and the refractive entities between the illumination source and the surface of interest make the illumination to the surface incoherent. For example, a laser diode coupled to a long multimode fiber can provide a spatially incoherent light provided that the different optical modes in the fiber are sufficiently temporally separated to reduce the temporal coherence. In another implementation, the illumination source is a broadband light source, such as a mercury lamp or the sun, with a bandpass filter HO nm bandpass region).

According to various implementations, a pupil ptychography imaging system comprises an aperture modulator which modulates apertures to N different locations at a surface located at the Fourier plane of an imager. In one case, the aperture modulator is configured to shift the transmissive (reflective) aperture(s) to N different locations in 1 second. In another case, the aperture modulator is configured to shift the transmissive (reflective) aperture(s) to N different locations in 0.5 seconds. In another case, the aperture modulator is configured to shift the transmissive (reflective) aperture(s) to N different locations in 0.1 seconds.

According to various implementations, a pupil ptychography imaging system comprises a first imager that acquires a sequence of N limited aperture images. In some implementations, N is in a range of 30-60. In another implementation, N is in a range of about 100-200. Generally the more severe the aberration, the higher the number N of limited aperture images would be used. According to moving sample implementations, a pupil ptychography imaging system comprises a second imager that acquires, in parallel (i.e. during image acquisition cycle), unmodulated images.

In certain implementations, the aperture modulator is in the form of an SLM that be digitally addressed to quickly shift a transmissive (reflective) aperture(s) across its display. A commercially-available example of an SLM is the LC-R 720 made by HOLOEYE®. In implementations where the aperture modulator is an SLM, N is the number of total shifted SLM admittance functions. Generally an SLM comprises an SLM display with discrete display elements. Each discrete SLM element can be set to function as an aperture (aperture setting) or to function as the area surrounding the aperture (field setting). In some aspects, an SLM display element in an aperture setting is transparent or nearly transparent to pass incident light and a display element in a field setting may block/reflect or nearly bock/reflect incident light. In other aspects, certain SLM display elements may be reflective. In these cases, a display element in the aperture setting is oriented at a (first) angle to reflect incident light to the next optical element in the optical arrangement and a display element in a field setting is oriented at a different (second) angle that reflects incident light away from the next optical element. In these aspects, the SLM display can generate an aperture at one or more SLM display elements by setting these display elements in an aperture setting and/or setting the surrounding display elements in a field setting. At different image acquisition times, $t_i$, different sets of one or more display elements are at appropriate settings to generate the aperture at the corresponding aperture location. In one case, the SLM display may have a refresh rate in the range of 30 per second to 100 per second. In another case, the SLM display may have a refresh rate in the range of 100 per second to 200 per second.

In certain implementations, the aperture modulator is the form of an LCoS display. The LCoS display is a reflective display having a plurality of reflective display elements. An example of a commercially-available LCoS display is the reflective SLM, Pluto, phase only LCoS, 8 μm pixel size, 1080×1920 pixels display by HOLOEYE®.

In certain implementations, the aperture modulator is the form of a DMD. The DMD comprises an optical semiconductor chip having on its surface multiple microscopic micromirrors. In certain aspects, each micromirror can be individually rotated to an angle, α. In this way, each micromirror can be transitioned to either an aperture setting at angle, α, or to a field setting at no rotation, or visa versa. Although these micromirrors are usually arranged in a rectangular array (dimensions o×p), other arrangements may be used. In certain aspects, each micromirror of the DMD may correspond to one or more light detector pixels. In one case, one or more of the micromirrors in the aperture setting may be oriented so that an optical axis orthogonal to the surface of the micromirror is oriented at an angle, a, from the Fourier plane.

An imager of a pupil ptychography imaging system generally includes at least one image sensor configured to detect light and output a data signal with image data of the intensity distribution (also referred to herein as a "light intensity distribution," or simply as an "image") over the sensing surface of the image sensor. The image data output from an image sensor is transmitted (or "sent" or "communicated") in a signal to image sensor(s) to one or more processors. The image sensor(s) acquire an image by measuring an intensity distribution of light incident its sensing area during an exposure time. Some examples of suitable image sensors are CMOS sensors, a charge-coupled device (CCD), and other similar devices. In one embodiment, an image sensor is a CMOS having a pixel size 11 μm such as the pco dimax HS4. In certain implementations, each image sensor of the first imager and/or second imager is a monochromic light detector. In some cases, one of the imagers of the system may be capable of high-speed capturing of a sequence of images, which may be particularly useful in retinal imaging, for example. In one case, an imager may be configured to acquire images at about 200 frames/second. In one case, an imager may be configured to acquire images at about 100 frames/second. In one case, an imager may be configured to acquire images at about 500 frames/second. An example of an imager capable of high-speed capturing is a high-speed digital camera such as, for example, the 340M-CL Fast Frame Rate CCD Camera made by Thorlabs.

Figure 3:
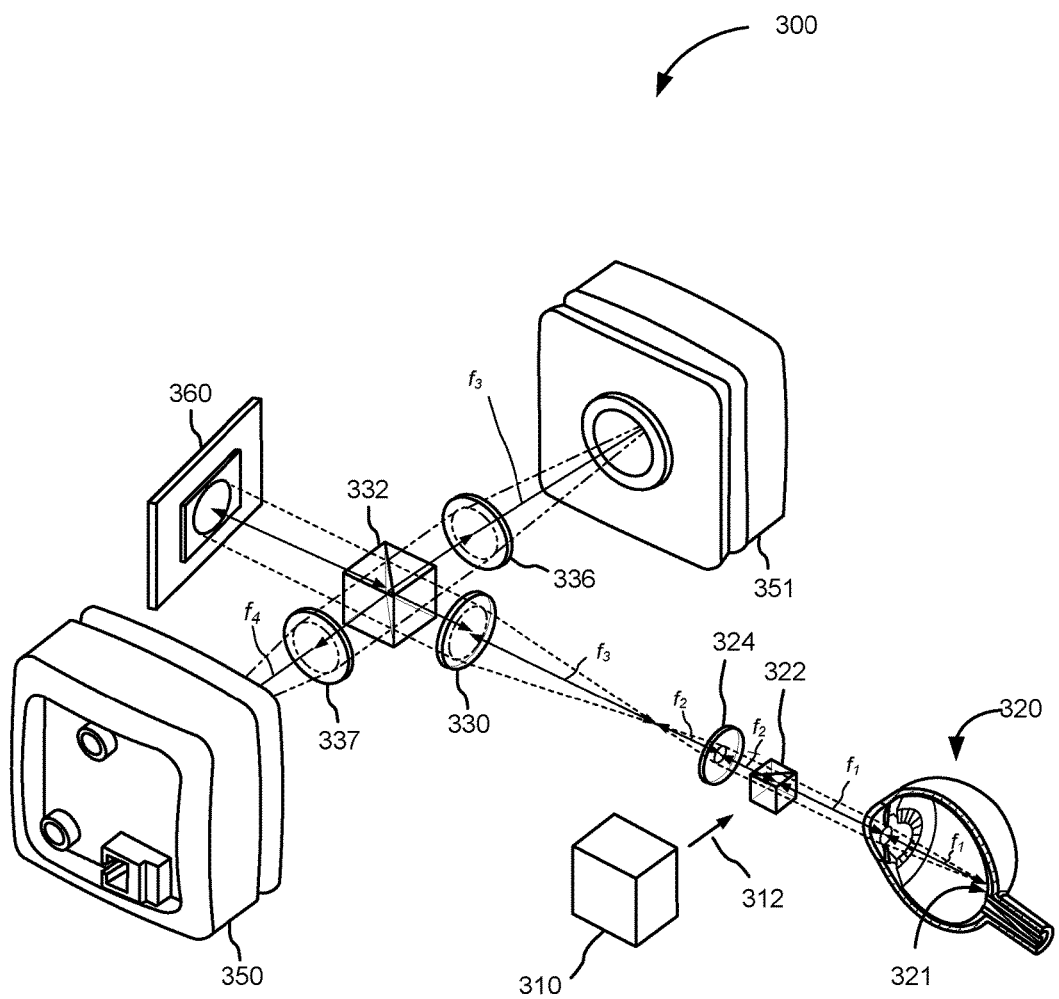
FIG. 3 is a schematic diagram of components of a pupil ptychography imaging system implemented for retinal imaging, according to embodiments.
Figure 4:
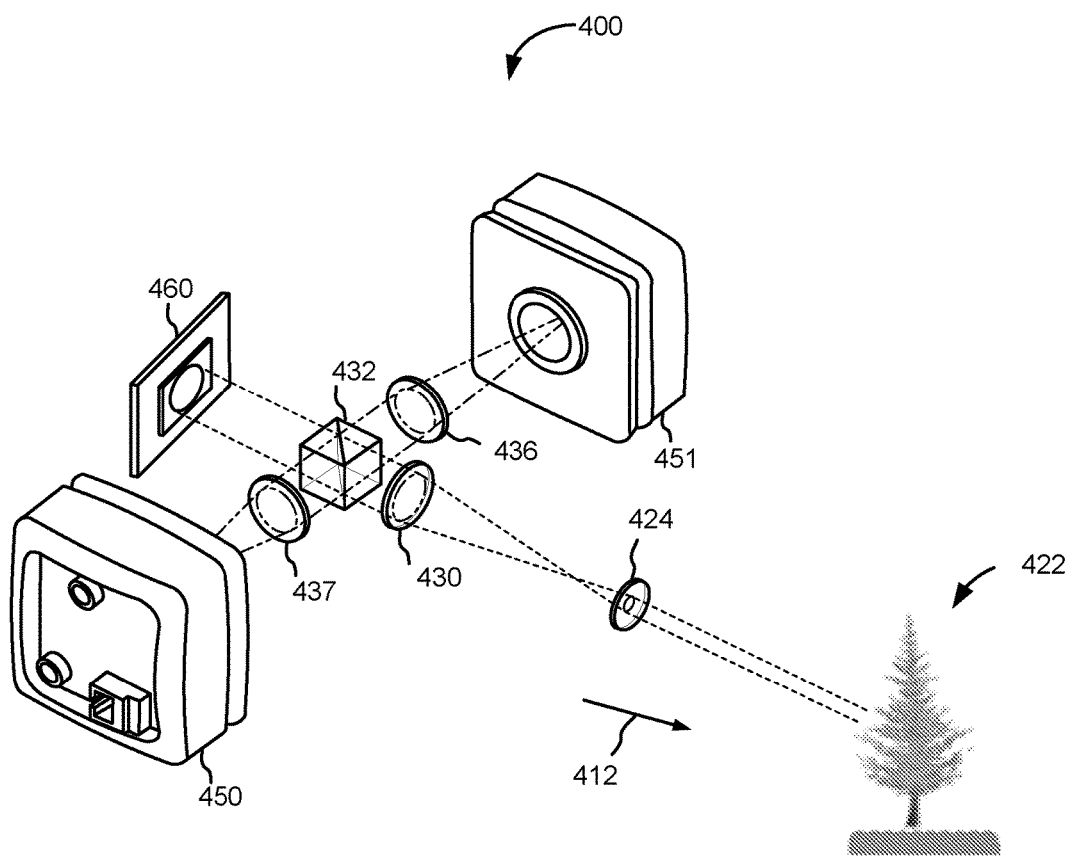
FIG. 4 is a schematic diagram of components of a pupil ptychography imaging system implemented for imaging of a natural scene, according to embodiments.

In certain implementations such as the examples shown in FIGS. 3 and 4, the pupil ptychography imaging system includes as first imager and a second imager. The image sensor(s) of the first imager are configured to acquire limited-aperture images and a full aperture image of the sample, and the second imager is configured to acquire an unmodulated image of the sample during an image acquisition cycle. Optionally, the image sensor(s) of the first imager are configured to acquire a sequence of N limited-aperture images based on a first aperture size and capture a limited aperture image of the aperture based on a second aperture size that is larger than the first aperture size.

According to various embodiments, the pupil ptychography imaging system includes optical components (e.g., beam splitters, objective lenses and/or other lenses, etc.) configured to propagate light reflected from the sample to the aperture modulator, from the aperture modulator to a first imager. Optionally, the optical components may also propagate light reflected from the sample to a second imager. In some cases, the optical components may be in a 4f or 6f arrangement that will allow for the modulation of the spatial spectrum using an aperture modulator that modulates aperture(s) at the Fourier plane of an imager. Examples of optical components are described with respect to FIGS. 3 and 4.

The one or more processor(s) 22 of the computing device 20 and, additionally or alternatively, other processor(s) of the pupil ptychography imaging system 10 (e.g., a processor of the external computing system 60) execute instructions stored on a computer readable memory (e.g., the internal memory 24 or external memory 70) to perform operations of the pupil ptychography imaging system 10. For example, the one or more processor(s) 22 of the computing device 20 may send control signals to the aperture modulator 32 to modulate apertures at different locations and may send control signals to the imager(s) 36 to activate exposure times to take intensity measurements to capture images during image acquisition. The one or more processor(s) 22 of the computing system 20 may also perform operations of the pupil ptychography imaging method to process the intensity measurements to determine the aberration of the optical system and an aberration-free image of the sample. An example of pupil ptychography imaging method is described with respect to FIG. 5. FIG. 6 illustrates an example of a phase retrieval procedure that can be used by the pupil ptychography imaging method in FIG. 5.

According to certain implementations, the computing device of a pupil ptychography imaging system can perform parallel image processing. To perform parallel image processing, the computing device generally includes at least one processor (or "processing unit"). Examples of processors include, for example, one or more of a general purpose processor (CPU), an application-specific integrated circuit, an programmable logic device (PLD) such as a field-programmable gate array (FPGA), or a System-on-Chip (SoC) that includes one or more of a CPU, application-specific integrated circuit, PLD as well as a memory and various interfaces. In some cases, the computing device is in communication with at least one internal memory device. The internal memory device can include a non-volatile memory array for storing processor-executable code (or "instructions") that is retrieved by the processor to perform various functions or operations described herein for carrying out various logic or other operations on the image data. The internal memory device also can store raw and/or processed image data (including acquired images and aberration free images). In some implementations, the internal memory device or a separate memory device can additionally or alternatively include a volatile memory array for temporarily storing code to be executed as well as image data to be processed, stored, or displayed. In some implementations, the computing device itself can include volatile and in some instances also non-volatile memory.

Each of the communication interfaces 52, 62, 72, and 82 is in electrical communication with the computing device 20. The described electrical communication between components of the pupil ptychography imaging system 10 may be able to provide power and/or communicate data. The electrical communication between components of the pupil ptychography imaging system 10 described herein may be in wired form and/or wireless form.

In FIG. 1, the computing device 20 is in communication with the communication interface 52 which is in communication with the display 50. In certain implementations, the computing device 20 is configured or configurable by a user (also referred to herein as an "operator") to output raw data or processed data over the communication interface 52 for display on the display 50. In some implementations, the computing device 20 also can be configured or configurable to output raw data as well as processed data (for example, after image processing) over a communication interface 62 to an external computing system 60. Indeed, in some implementations, one or more of the pupil ptychography imaging operations can be performed by such an external computing system 60. In some implementations, the computing device 20 also can be configured or configurable by a user to output raw data as well as processed data over a communication interface 72 for storage in an external memory device 70.

In some implementations, the pupil ptychography imaging system 10 further includes one or more additional interfaces such as, for example, various Universal Serial Bus (USB) interfaces or other communication interfaces. Such additional interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with the computing device 20 over one or more of a variety of suitable interfaces and cables such as, for example, USB interfaces and cables, ribbon cables, Ethernet cables, among other suitable interfaces and cables.

The data signals output by the image sensors may in some implementations be mutliplexed, serialized or otherwise combined by a multiplexer, serializer or other electrical component of the imaging system before being communicated to the computing device. In certain implementations, the computing device can further include a demultiplexer, deserializer or other device or component for separating the image data from each of the image sensors so that the image frames can be processed in parallel by the controller.

Figure 2:
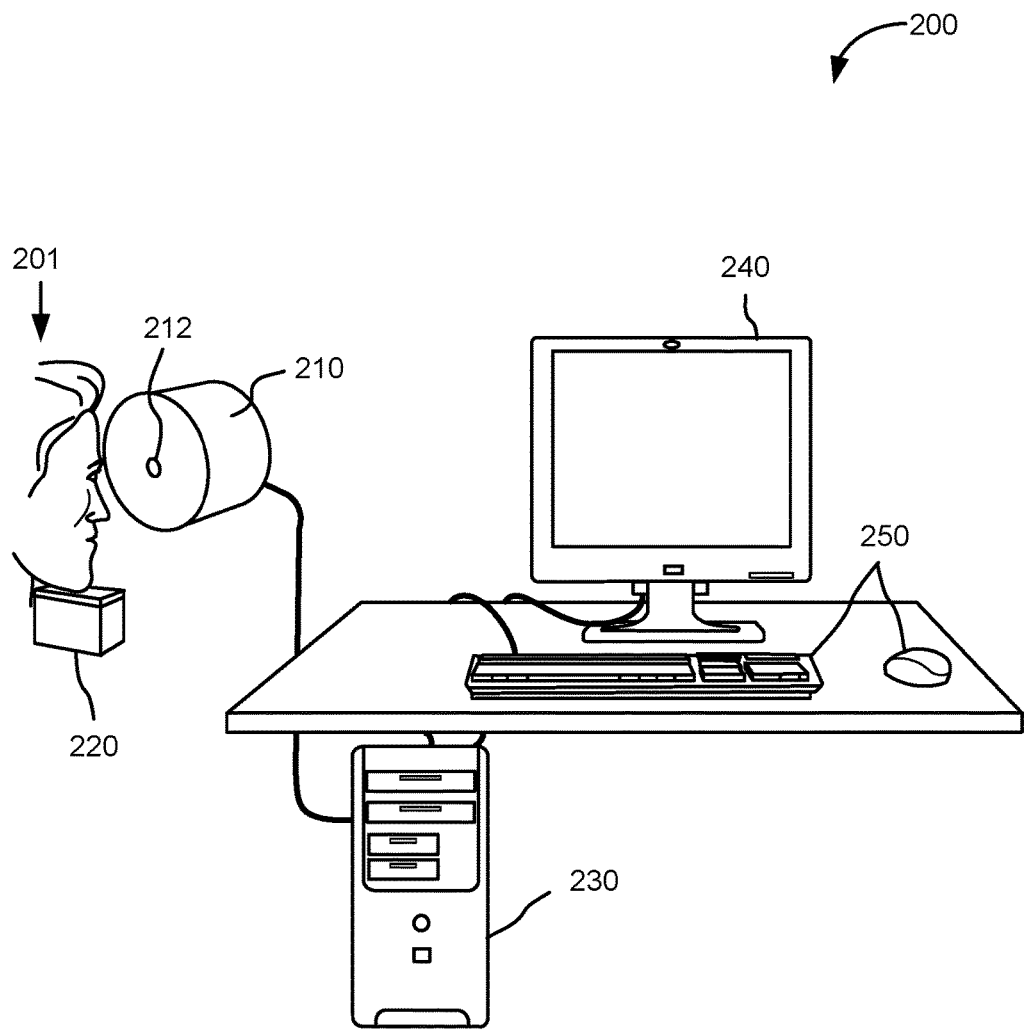
FIG. 2 is a schematic diagram of components of a pupil ptychography imaging system implemented for retinal imaging, according to embodiments.

Some examples of pupil ptychography imaging systems are shown in FIGS. 2, 3, and 4. Some of these pupil ptychography imaging systems have one or more components that are similar to those described with respect to pupil ptychography imaging system 10 in FIG. 1.

—Example of Retinal Imaging Configuration

FIG. 2 is a schematic diagram of components of a pupil ptychography imaging system 200 implemented for retinal imaging, according to embodiments. The illustrated pupil ptychography imaging system is configured for imaging a retinal surface of a moving in-vivo eye. At a high level, the pupil ptychography imaging system 200 is configured to illuminate the retina of an eye with monochromatic, spatially-incoherent illumination, capture a sequence of N limited-aperture retinal images during an image acquisition process, capture a full pupil image, capture unmodulated retinal images during an image acquisition process, determine the pupil function of the optical system based on the image data, and correct the full pupil image to generate a substantially aberration-free or aberration-free complex image of the retina. The optical system in this implementation includes the portion of the eye to the retina. For illustration purposes, pupil ptychography imaging system 200 is shown with a person 201 positioned during the image acquisition process.

The pupil ptychography imaging system 200 includes a casing 210 that contains components of the pupil ptychography imaging system 200 including, for example, an illumination source, optical components, an aperture modulator, and a first and second imager. The casing 210 has a transparent region 212 for allowing light from the illumination source inside the casing 210 to illuminate the retina of the eye of the person 201. For simplicity, the casing 210 is shown here in the shape of a cylinder and the transparent region 212 is circular. Other shapes can be used. The transparent region 212 may be an aperture filled with a transparent material or may be an open aperture. The pupil ptychography imaging system 200 is also shown with an optional chin rest 220 for positioning the person 201 and their eye at a certain distance from the collection optics inside the casing 210. The optional chin rest 220 can also help stabilize or prevent movement of the person 201 during the image acquisition process. The casing 210 may be mounted to the wall or placed on or mounted to a platform such as a desk, a stand, or a chair for receiving the person 201. The chin rest 220 may be mounted to the same object as the casing 210 or another object.

The pupil ptychography imaging system 200 also includes a computing device 230 having one or more processors and a computer readable medium (CRM), e.g., memory, in electronic communication with the one or more processors. The one or more processors execute instructions stored on the CRM to complete operations of a pupil ptychography imaging method. The pupil ptychography imaging system 200 also includes a display 240 and one or more input devices 250 (e.g., keyboard and mouse), both of which are in electronic communication with the computing device 230. The components of the pupil ptychography imaging system 200 inside the casing 210 are in electronic communication with the computing device 230 via wiring. Although many of the components of the pupil ptychography imaging system 200 are shown in electronic communication with each via wiring, it would be understood that the electronic communication between components of pupil ptychography imaging systems described herein can be in wired form, wireless form, or a combination thereof.

According to various embodiments, output from operations of the pupil ptychography imaging method such as an aberration-free or substantially aberration-free image of the retina can be displayed on a display such as the display 240 shown in FIG. 2. In FIG. 2, the one or more processors of the computing device 230 execute instructions stored on the CRM to generate display data that is transmitted in a signal to the display 240.

FIG. 3 is a schematic diagram of components of a pupil ptychography imaging system 300 implemented for retinal imaging, according to embodiments. The illustrated pupil ptychography imaging system is configured for imaging a retinal surface of a moving in-vivo eye. In one example, the components of pupil ptychography imaging system 300 may be an example of components that are contained in the casing of the system 200 shown in FIG. 2.

In FIG. 3, the pupil ptychography imaging system 300 comprises an illumination source 310, various optical components, a first imager 350 (e.g., high speed digital camera) for acquiring limited-aperture images and a full aperture image, a second imager 351 (e.g., high speed digital camera) for acquiring unmodulated image(s), and an aperture modulator 360 (e.g. spatial light modulator) for modulating apertures at the Fourier plane of the first imager 350. The pupil ptychography imaging system 300 is shown at an instant in time when the illumination source 310 is providing monochromatic, spatially-incoherent illumination 312 to the retinal surface 321 of the eye 320. The pupil ptychography imaging system 300 also includes various optical components that are configured to propagate light reflected from the retinal surface 321 and passing out the eye 320 to the second imager 351 and to the aperture modulator 360. The optical components are also configured to propagate light from the aperture modulator 360 to the first imager 350.

In FIG. 3, the illumination source 310 comprises an extended diffuse LED or an extended SLD coupled to a first end of a multimode fiber. The extended diffuse LED or extended SLD is designed to generate monochromatic, spatially-incoherent light. The multimode fiber may then be manipulated to point the opposing second end of the multimode fiber to direct monochromatic, spatially-incoherent illumination from the second end. In other implementations, other illumination sources may be used. An extended broadband light source such as a mercury lamp may be bandpass filtered to provide a short bandwidth (~10 nm), spatially incoherent illumination on the sample.

In FIG. 3, the optical components further comprise a first beam splitter 322, a first lens 324 has a focal length, $f_2$, a second lens 330 having a focal length, $f_3$, a second beam splitter 332, and a third lens 336 having a focal length, $f_3$, and a fourth lens 337 having a focal length, $f_4$. The optical components shown in FIG. 3 are in a 6f arrangement. The first beam splitter 322 is configured to reflect monochromatic, spatially incoherent light 312 from the illumination source 310 to the eye 320. The light propagates through the eye's media (e.g., cornea, aqueous, lens, and vitreous) and is reflected from the retinal surface 321 at the back of the eye 320. The reflected light from the retinal surface 321 is propagated back through the eye's media and to the first beam splitter 322. The first beam splitter 322 is further configured to transmit the part of the light reflected from the retinal surface 321 that is depolarized. An example of a commercially-available beam splitter that can be used is the polarizing beam splitter: PBS251 from Thorlabs. Some suitable beam splitters are polarizing beam splitters designed to reflect the component of the light with a particular polarization direction (e.g. 0 degrees) while transmitting the component with the perpendicular polarization direction (e.g. 90 degrees). Only the part of light that is reflected by the retina that is depolarized will be able to pass through the beam splitter to be captured by the system. Suitable beam splitters are commercially available. Light from the eye 320 is transmitted through the first beam splitter 322 to the first lens 324 (e.g., objective lens) and to the second lens 330 which collimates the light. The second beam splitter 332 reflects a component of the light propagated from the second lens 330 to the third lens 336, which focuses the light at the second imager 351. The second beam splitter 332 transmits another component of the collimated light from the second lens 320 to the aperture modulator 360 which has a display surface at the Fourier plane of the first imager 350. Light incident the aperture modulator 360 within the admittance circular pupil function is reflected to the second beam splitter 332. The second beam splitter 332 reflects the light from the aperture modulator 360 to the fourth lens 337 which focuses the light to the first imager 350. Optionally, the pupil ptychography imaging system 300 may include an adjustable focusing lens between the first beam splitter 322 and the eye 320. In addition or alternatively, the lens 324 may be translated axially to move the system's focal plane around the eye's retinal plane.

During an exemplary image acquisition process of the pupil ptychography imaging system 300, the eye 320 of the patient is positioned in front of the first beam splitter 322 or the first beam splitter 322 is positioned in front of the eye 320. The illumination source 310 receives a control signal to turn on the monochromatic spatially-incoherent illumination 312. Control signals are sent to the first imager 350, the second imager 351, and the aperture modulator 360 to synchronize image acquisition of the various limited aperture images and full aperture image taken by the first imager 350 and the unmodulated images taken by the second imager 351. The first imager 350 and second imager 350 are generally configured to capture aberrated images emerging from the retinal surface 321 of the eye 320 through the optical system of the eye 320. The second imager 351 captures unmodulated images. In parallel, the first imager 350 captures a sequence of N limited-aperture images with the pupil reduced by the aperture modulator 360 in the Fourier plane of the first imager 350. The second imager 351 also captures a full aperture image with an aperture equivalent to the desired system NA. The first imager 350, the second imager 351, and the aperture modulator 360 are synchronized to capture images at the same time while the aperture modulator 360 displays shifted apertures on the Fourier plane of the first imager 350 for each limited aperture image being captured. During an image acquisition cycle, a sequence of N limited-aperture images is captured by the first imager 350 corresponding to N different aperture locations at the Fourier plane, at least one full pupil image is captured by the first imager, and a sequence of unmodulated images is captured by the second imager 351. In one example, N can be in a range of 30 to 60. In another example, N can be from 100 to 200. Optionally, the first imager 350 may capture N limited-aperture images based on a first aperture size and captures another limited-aperture image based on a second aperture size larger than the first aperture size.

Depending on the optical system being measured by a pupil ptychography imaging system of a particular implementation, the images (also referred to as intensity measurements or intensity distributions) taken by the imager(s) may have different exposure times. In some cases, the measurements may have exposure times with long durations such as when imaging natural scenes, from 10 milliseconds to 10 seconds. In other cases, such as when imaging an in-vivo eye, the measurements are performed quickly such as one image per 1-10 milliseconds. In the retinal imaging case, the images captured in the sequence of N limited aperture images may have relative shifts with respect to one another due to the eye's movement during image acquisition. These images are then processed using the pupil ptychography imaging method such as described with respect to FIG. 5 to reconstruct the pupil function of the optical system and an aberration-removed image of the surface of interest.

According to various implementations, a pupil ptychography imaging system implements one or more processors (internal/external) to interpret and process the image data sampled during an image acquisition cycle to generate processed image data. In some implementations, the processor(s) are configured or configurable to perform operations on the image data of a sequence of intensity images to reconstruct a pupil function of the optical system and corresponding aberration, and remove the aberration from a full pupil image of the sample to generate a substantially aberration-free or aberration-free complex image.

In some implementations, a pupil ptychography imaging system is configured to image a moving sample. In these implementations, the pupil ptychography imaging system includes two imagers (e.g., cameras) that are configured to capture the aberrated image emerging from the retinal surface of the eye through the optical system of the eye, or any other optical system and a surface of interest such as a natural scene imaged through a camera lens. One of the imagers captures unmodulated images. In parallel, the other imager captures modulated images either a full aperture image or images with the pupil reduced by the aperture modulator, e.g., SLM, in the Fourier plane of the other imager. These two imagers are synced to captures images at the same time while the aperture modulator displays a variably shifted aperture on the Fourier plane for each modulated image captured. Depending on the optical system being measured, these measurements can have long durations or they need to be performed quickly for cases such as imaging an in-vivo eye. In such a retinal imaging case, the images captured in a sequence may have relative shifts with respect to one another due to the eye's movement. This shift can be correctly registered by using the full-aperture images since these images are not modulated in any way other than by the eye's movement. These full-aperture images are then processed using the pupil ptychography imaging method as described below with reference to FIG. 5 to reconstruct the pupil function of the optical system and an aberration-removed image of the surface of interest.

—Example of Natural Scenes Imaging Configuration

FIG. 4 is a schematic diagram of components of a pupil ptychography imaging system 400 implemented for imaging of a natural scene 422, according to embodiments. The pupil ptychography imaging system 400 comprises various optical components, a first imager 450 (e.g., high speed digital camera) for acquiring N limited-aperture images and a full aperture image, a second imager 451 (e.g., high speed digital camera) for acquiring unmodulated images, an aperture modulator 460 (e.g. spatial light modulator) for modulating apertures at the Fourier plane of the first imager 450. The pupil ptychography imaging system 400 is shown at an instant in time when spatially-incoherent illumination 412 is provided to the natural scene 422 being imaged by the system 400. The various optical components are configured to propagate light reflected from the natural scene 422 to the second imager 451, propagate light reflected from the natural scene 422 to the aperture modulator 460, and propagate light from the aperture modulator 460 to the first imager 450. Although not shown, the optical components further include a bandpass filter configured to filter the light reflected from the natural scene. A bandpass filter with a bandwidth of about 10 nm would be suitable.

In FIG. 4, the optical components comprise a first lens 424, a second lens 430, a beam splitter 432, and a third lens 436, and a fourth lens 437. During image acquisition, spatially-incoherent illumination 412 illuminates the surface (s) of interest of the natural scene 422. Flight reflected from the surface(s) propagate to the first lens 424 (e.g., objective lens) and to the second lens 430 which collimates the light. The beam splitter 432 reflects a component of the collimated light from the second lens 420 to the third lens 436, which focuses the light to the second imager 451. The beam splitter 432 transmits another component of the collimated light from the second lens 420 to the aperture modulator 360 which has a display surface at the Fourier plane of the first imager 450. Light incident the aperture modulator 440 within the admittance circular pupil function is reflected to the beam splitter 432. The beam splitter 432 reflects light from the aperture modulator 440 to the fourth lens 437, which focuses light propagated from the beam splitter 432 to the first imager 450.

During an exemplary image acquisition process of the pupil ptychography imaging system 400, one or more control signals are sent by a processor(s) to the first imager 350, the second imager 351, and the aperture modulator 460 to synchronize image acquisition of the various limited aperture images and full aperture image taken by the first imager 450 and the unmodulated images taken by the second imager 451. The first imager 450 and second imager 450 are generally configured to capture aberrated images emerging from the surfaces of the natural scene 422 through the optical system of the natural scene. The second imager 351 captures one or more unmodulated images of the natural scene 422, and in parallel, the first imager 350 captures a sequence of N limited-aperture images of the natural scene 422 with the pupil reduced by the aperture modulator 360 in the Fourier plane of the first imager 450. The second imager 451 also captures a full aperture image of the natural scene 422 with an aperture equivalent to the desired system NA. The first imager 450, the second imager 451, and the aperture modulator 460 are synchronized to capture images at the same time while the aperture modulator 460 displays shifted apertures on the Fourier plane of the first imager 450 for each limited aperture image being captured. During an image acquisition cycle, a sequence of N limited-aperture images of the natural scene 422 is captured by the first imager 450 corresponding to N different aperture locations at the Fourier plane, at least one full pupil image is captured of the natural scene 422 by the first imager, and unmodulated images of the natural scene 422 is captured by the second imager 451. In one example, N can be from 30 to 60. In another example, N can be from 100 to 200. Optionally, the first imager 450 may capture N limited-aperture images based on a first aperture size and captures another limited-aperture image based on a second aperture size larger than the first aperture size.

In various implementations, the second imager captures one or more unmodulated images. In one implementation, the second imager captures N unmodulated images. In another implementation, the second imager captures one unmodulated image. In another implementation, the second imager captures two unmodulated images. In another implementation, the second imager captures less than N unmodulated images.

III. Pupil Ptychography Methods

In various embodiments, pupil ptychography methods capture a sequence of N limited-aperture images and a full aperture image of a sample that is illuminated by monochromatic, spatially-incoherent illumination, computationally determine the aberration of the optical system, and deconvolve the full aperture image to remove the aberration. In embodiments with a moving sample, unmodulated aperture images are also captured in parallel in order to correct for the sample's motion. When used to image a wide field-of-view, the aberration of the optical system and, by extension, the pupil function can be expected to show spatial variations and the aberration may not be the same for different regions within the field-of-view. In some cases, a field-of-view is considered to be wide if larger than 1 degree of visual field. In this case, the entire field-of view of each of the captured images is segmented into smaller tile images and the aberration within each tile is assumed to be constant.

With a moving sample, images may shift spatially between sample times of a sequence of images. In an optional motion registration operation, the shifts in the N limited-aperture images and the full aperture image can be correctly registered using the corresponding unmodulated images since these images not modulated in any way other than by sample movement. Registration is an optional operation implemented prior to characterizing the aberration of the optical system since shifting of the captured images may incorrectly encode aberration information in the reconstruction process.

During aberration characterization, the aberration of the optical system is determined. The pupil ptychography methods use either one of the N limited-aperture images or a slightly expanded limited aperture image as ground-truth.

The ground truth image is then used to deconvolve all the limited-aperture images to recover a point-spread function (PSF) associated with each limited aperture. These recovered PSFs are of intensity information of the various low-pass filtered versions of the actual complex PSF of the system with the full aperture opened. The pupil ptychography methods use a phase retrieval process to synthesize these low-pass PSFs into the full-sized complex pupil function. After reconstructing the complex pupil function, the PSF associated with the complex pupil function can calculated, which can then be used to deconvolve from the full-aperture image to obtain an aberration-removed image of the sample.

Figure 5:
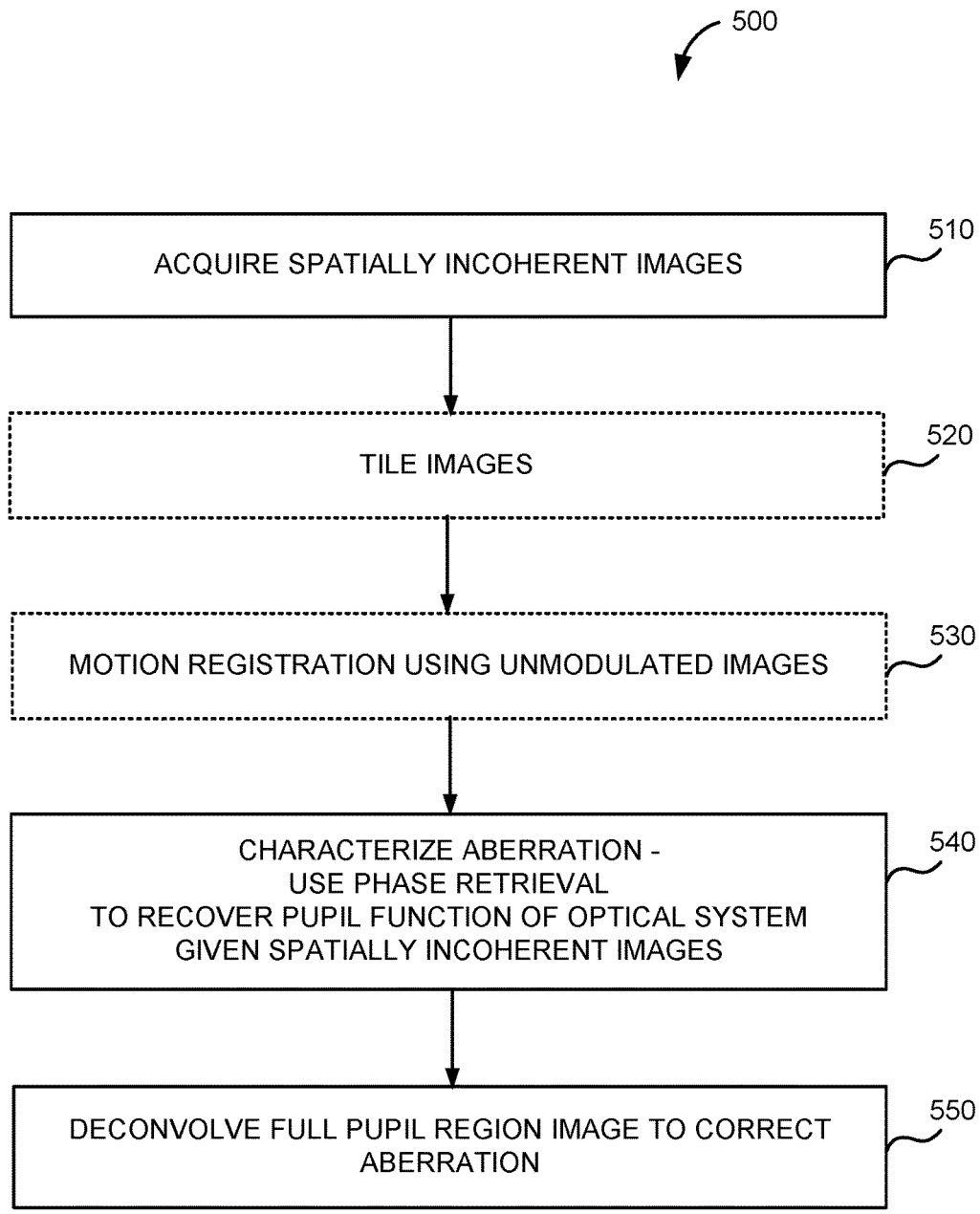
FIG. 5 depicts a flowchart of operations of a pupil ptychography method, according to various implementations.
Figure 6:
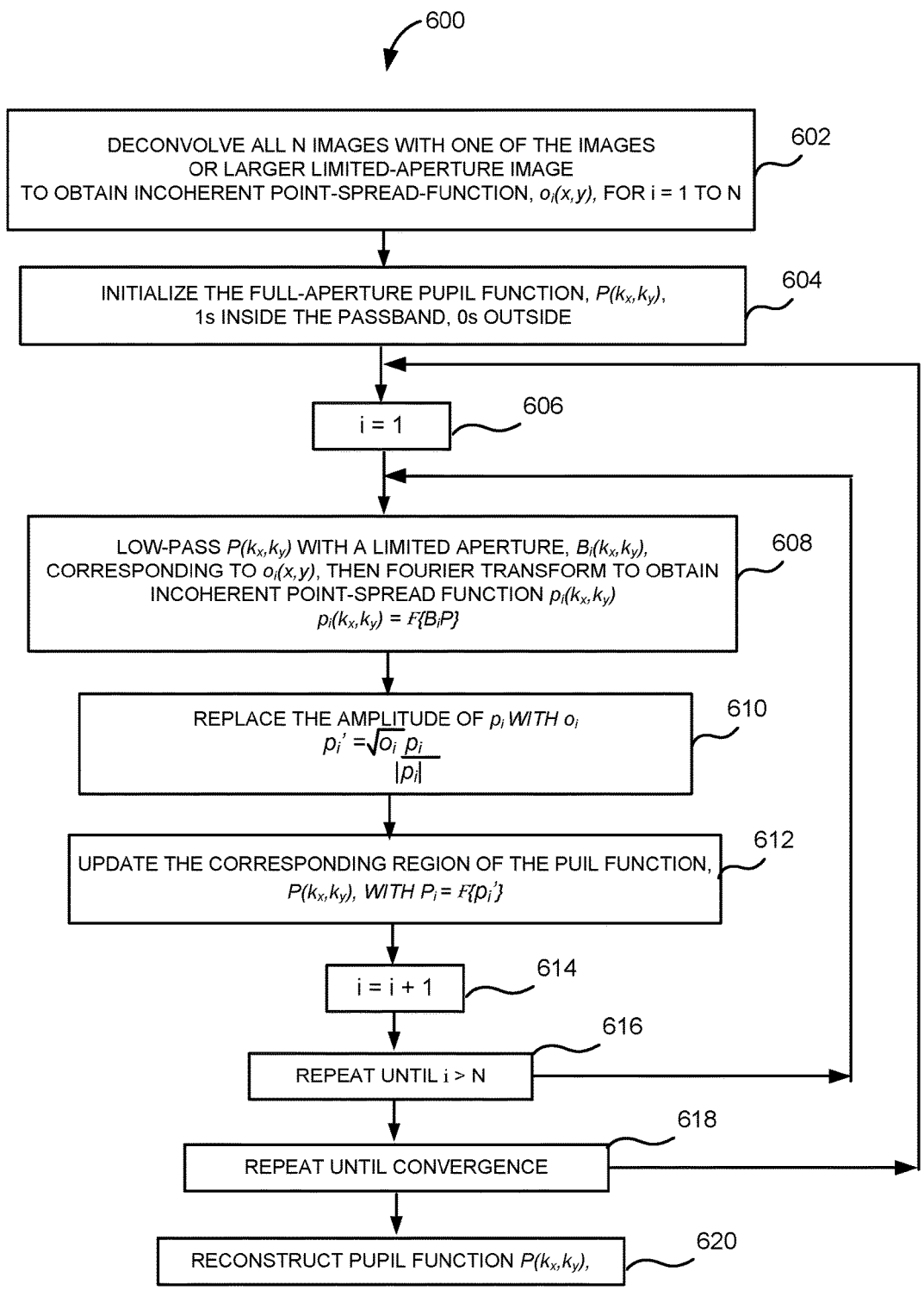
FIG. 6 depicts a flowchart of operations of an aberration characterization process of a pupil ptychography method, according to an implementation.

FIG. 5 depicts a flowchart 500 of operations of a pupil ptychography method, according to various implementations. At operation 510, the pupil ptychography method captures aberrated images of the sample illuminated with monochromatic, spatially-incoherent illumination during each image acquisition cycle. During this cycle, the sample may be continuously illuminated or the sample may be illuminated during the exposure times during each image capture. In implementations with a non-moving sample and with a moving sample, a first sequence of N limited-aperture images of the sample and a full aperture image of the sample is captured. The full-aperture image is the image from which the optical system aberration will be removed. Generally, the N limited aperture image and the full aperture image are captured by a first imager synchronized with an aperture modulator that forms apertures at different locations on the Fourier plane of the first imager. Optionally, the first imager also captures an additional limited-aperture image corresponding to a second aperture size of the aperture modulator that is larger than the first aperture size of the aperture modulator corresponding to the N limited aperture images. In an implementation with a moving sample, a sequence of N unmodulated images is also captured in parallel with the N limited-aperture images. Generally, the N limited-aperture images and the N unmodulated images are captured by the first imager and a second imager respectively, which are synchronized to capture the different sequences of images in parallel. That is, the first imager captures a modulated image during the same exposure time as the second imager captures an unmodulated image.

In one implementation, the pupil ptychography system includes a first imager and a second imager and implements the first imager to take modulated images if the sample is not moving and implements the first imager to take modulated images and the second imager to take unmodulated images in parallel if the sample being imaged is moving. Alternatively, both the first imager to take modulated images and second imager to take unmodulated images and then the method only uses the unmodulated images to correct for motion if the method makes a determination that the sample is moving.

At operation 520, optionally (denoted by dashed line) the pupil ptychography method segments the image data of each of the full field-of-view images captured during operation 510 into a matrix of tile images using one or more processors. In one case, the full field-of-view may be segmented into equivalent portions based on keeping each portion less than a size within which the aberration can be assumed to be constant. For example, the full field-of-view may be segmented to keep the field of view of each tile image within a predetermined size. The predetermined size may be, for example, 1 degree, 2 degrees, or 3 degrees of visual field. In one implementation, operation 520 may be invoked if the method determines that the field-of-view is greater than a threshold size. Some examples of threshold sizes are 1 degree, 2 degrees, or 3 degrees of visual field etc.

In the case a moving sample, the limited-aperture images captured at different sample times may have relative spatial shifts with respect to one another due to the sample's movement. These shifts can be correctly registered by using the unmodulated images since these images are not modulated in any way other than by the movement of the sample. At operation 530, optionally (denoted by dashed line) if the sample is considered to be moving, the pupil ptychography method registers the motion of the sample using the unmodulated images captured during operation 510. To register the motion of the sample, a spatial shift of each one of the sequence of N limited-aperture images is determined by comparing the spatial location of the corresponding unmodulated image taken at the same sample time to the unmodulated image taken at the first sample time. For example, a spatial shift of the $5^{th}$ limited-aperture image taken at $t=t_5$ is determined by comparing the location of the $5^{th}$ unmodulated image at $t=t_5$ to the location of the first unmodulated image taken at $t=t_1$ and so on. The pupil ptychography method can then correct each limited-aperture image based on the determined spatial shift.

In one implementation, the pupil ptychography method compares two or more of the unmodulated images to determine whether the sample is moving. If movement exists, then the method proceed with operation 530 to correct the limited-aperture images for motion. In other implementations, the pupil ptychography method may always correct for movement.

At operation 540, the pupil ptychography method uses one or more processors to characterize the aberration of the optical system using image data of the spatially incoherent images collected in operation 510. If each of the captured images were tiled in the optional operation 520, then operation 540 is performed to determine an aberration based on each of the tile regions. FIG. 6 depicts a flowchart that describes details of an example of sub-operations of operation 540.

At operation 550, the pupil ptychography method uses one or more processors to deconvolve the full pupil (full aperture) image captured in operation 510 to correct for the aberration determined in operation 540. If each of the captured images were tiled in the optional operation 520, then operation 550 decolvolves each of the tile images of the full aperture image to correct for aberration in each tile region. Then, the pupil ptychography method mosaics the aberration-free or substantially aberration free tile images together to form a full field-of-view image that is aberration-free or substantially aberration free.

In various implementations, a deconvolution operation is used. A blind deconvolution operation can be used when the pupil function of the system. Non-blind deconvolution is used when you have knowledge of the pupil function. Some examples of non-blind deconvolution techniques that can be used include Tikhonov regularization, Wiener deconvolution, block matching and 3D filtering (BR3D).

FIG. 6 depicts a flowchart 600 of sub-operations of aberration characterization process of a pupil ptychography method, according to an implementation.

At operation 602, the pupil ptychography method deconvolves each of the sequence of N limited-aperture images based on a ground truth image to obtain an incoherent point-spread-function, $o_i(x, y)$, for i=1 to N. In one example, the ground truth image is one of the limited-aperture images based on the first aperture size. In another example, the ground truth image is the limited-aperture image based on the second aperture size larger than the first aperture size.

At operation 604, the pupil ptychography method initializes a full-aperture pupil function, $P(k_x,k_y)$, with 1s inside the passband and 0s outside the passband. The pass band is defined by the full aperture's NA in the Fourier domain.

At operation 606, the pupil ptychography method initializes the counter i=1.

The incoherent point-spread-functions, $o_i(x, y)$, of the N limited aperture images are the intensity information of the various low-pass filtered versions of the actual complex point spread function of the optical system with the full aperture opened.

At operation 608, the method determines the low-pass filtered version of the full-aperture pupil function, $P(k_x,k_y)$, with a limited aperture, $B_i(k_x,k_y)$, that corresponds to the incoherent point-spread-functions, $o_i(x, y)$. Then, the low-pass filtered version with a limited aperture, $B_i(k_x,k_y)$, is Fourier transformed to obtain the coherent point-spread-function $p_i(x, y)$ according to: $p_i(x, y)=F\{B_iP\}$. The incoherent PSF is the absolute squared of the coherent point spread function.

At operation 610, the method replaces the amplitude of $p_i(x, y)$ with the square root of the incoherent point-spread-function value, $o_i(x, y)$ using:

$$p'_i = \sqrt{o_i}\,\frac{p_i}{|p_i|}.$$

At operation 612, the method updates the corresponding region of the full-aperture pupil function, $P(k_x,k_y)$, with $P_i$. $P_i$ is the Fourier transform of $p'_i$ according to: $P_i=F\{p'_i\}$.

At operation 614, the pupil ptychography method increments the counter i=i+1.

At operation 616, the pupil ptychography method returns to repeat operations 608, 610, 612, 614 until i is greater than N. If i is greater than N at operation 610, then the method goes on to operation 618 to determine whether the solution has converged. If it is determined that the solution has not converged at operation 618, the method returns to operation 606 to initialize the counter to i=1. If it is determined that the solution has converged at operation 618, the method has reconstructed the solution for the pupil function P $(k_x,k_y)$ at operation 620. The method determines the aberration for the full-aperture image based on the reconstructed pupil function $P(k_x,k_y)$. If the operational tiling operation was performed on the image, the method determines the aberration for the tile image based on the reconstructed pupil function $P(k_x,k_y)$ for the tile region.

Modifications, additions, or omissions may be made to any of the above-described embodiments without departing from the scope of the disclosure. Any of the embodiments described above may include more, fewer, or other features without departing from the scope of the disclosure. Additionally, the steps of the described features may be performed in any suitable order without departing from the scope of the disclosure.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a CRM such as a random access memory (RAM), a read only memory (ROM), a magnetic medium such as a hard-drive or a floppy disk, or an optical medium such as a CD-ROM. Any such CRM may reside on or within a single computational apparatus, and may be present on or within different computational apparatuses within a system or network.

Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A pupil ptychography system comprising:
    an aperture modulator configured to modulate apertures at a Fourier plane of a first imager;
    the first imager configured to acquire a full pupil image of a sample being incoherently illuminated by a light source during operation, and configured to acquire a sequence of N limited-aperture images of the sample while the aperture modulator modulates a first aperture to N locations at the Fourier plane of the first imager;
    one or more optical components configured to propagate light reflected from the sample to the aperture modulator and propagate light from the aperture modulator to the first imager; and
    at least one processor configured to:
        use the N limited-aperture images to recover a pupil function of an optical system in an optical path between the sample and the first imager; and
        deconvolve the full pupil image of the sample using the recovered pupil function to generate a substantially aberration-free full pupil image of the sample.

2. The pupil ptychography system of claim 1,
    further comprising a second imager in communication with the at least one processor,
        wherein the optical components are further configured to propagate light reflected from the sample to the second imager,
        wherein the second imager is configured to acquire, in parallel with the first imager, one or more unmodulated images of the sample, and
        wherein the processor is further configured to modify the N limited-aperture images and the full aperture image to correct for motion based on the one or more modulated images.

3. The pupil ptychography system of claim 1, wherein the first imager is further configured to acquire another limited aperture image while the aperture modulator modulates a second aperture at the Fourier plane of the first imager, wherein the second aperture is larger than the first aperture.

4. The pupil ptychography system of claim 3, wherein the second aperture is at least 10% larger than the first aperture.

5. The pupil ptychography system of claim 3, wherein the second aperture is at least 5% larger than the first aperture.

6. The pupil ptychography system of claim 1,
wherein the at least one processor is further configured to
segment each of the limited-aperture images into tiles regions;
recover a tile pupil function for each of the tile regions; and
combine the recovered tile pupil functions to generate the pupil function of the optical system.

7. The pupil ptychography system of claim 1, further comprising an illumination source configured to provide monochromatic, incoherent illumination to the sample during operation.

8. The pupil ptychography system of claim 1, further comprising an illumination source configured to provide monochromatic, incoherent illumination of each of a red wavelength, a green wavelength, and a blue wavelength to the sample during operation.

9. The pupil ptychography system of claim 1, wherein the at least one processor is further configured to send signals to the first imager and the aperture modulator to synchronize the sampling times of the first imager with times for modulating the apertures at the Fourier plane.

10. The pupil ptychography system of claim 1, wherein the aperture modulator is a spatial light modulator configured to digitally address to shift the first aperture to the N different locations across the Fourier plane.

11. The pupil ptychography method of claim 1, wherein the aperture modulator is a digital micromirror device.

12. A pupil ptychography method comprising:
receiving, from a first imager, a sequence of N limited-aperture images of a sample being incoherently illuminated, the N limited-aperture images are acquired, by the first imager, while an aperture modulator sequentially modulates a first aperture at N different locations at the Fourier plane of the first imager and one or more optical components propagate light reflected from the sample to the aperture modulator and propagate light from the aperture modulator to the first imager;
receiving a full pupil image of the sample from the first imager, the full pupil image acquired while the sample is incoherently illuminated by a light source;
recovering a pupil function of an optical system in an optical path between the sample and the first imager the sequence of N limited-aperture images; and
deconvolving the full pupil image of the sample using the recovered pupil function to generate a substantially aberration-free full pupil image of the sample.

13. The pupil ptychography method of claim 12, sending one or more signals to the aperture modulator and the first imager to synchronize generation of the first aperture by the aperture modulator at N different locations of the Fourier plane of the first imager with the acquisition of N limited aperture images of the sample.

14. The pupil ptychography method of claim 12, further comprising receiving another limited aperture image, from the first imager, the other limited aperture image acquired while a second aperture was modulated, by the aperture modulator, at the Fourier plane of the first imager.

15. The pupil ptychography method of claim 12,
further comprising segmenting each of the sequence of N limited-aperture images into tiles regions; and
wherein recovering the pupil function comprises recovering a tile pupil function for each of the tile regions and combining the recovered tile pupil functions to generate the pupil function of the optical system.

16. The pupil ptychography method of claim 12, wherein the first imager acquires images while the sample is illuminated by monochromatic, incoherent illumination.

17. The pupil ptychography method of claim 12, comprising:
receiving, from a second imager, one or more unmodulated images of the sample being incoherently illuminated; and
correcting the N limited-aperture images for motion based on the one or more modulated images.

18. The pupil ptychography method of claim 12, comprising:
receiving, from the first imager, another limited aperture image based on a second aperture larger than the first aperture; and
initializing the pupil function based on the other limited aperture image received from the first imager.

* * * * *